United States Patent [19]
Takeuchi et al.

[11] Patent Number: 5,541,303
[45] Date of Patent: Jul. 30, 1996

[54] 3,4'-DIDEOXYMYCAMINOSLTYLONOLIDE DERIVATIVE AND PROCESS FOR PRODUCING THE SAME

[75] Inventors: Tomio Takeuchi, Higashi Gotanda; Sumio Umezawa, Shinjuku; Osamu Tsuchiya, Eda Higashi; Shunji Kageyama, Tsukuba; Toshiaki Miyake, Yokohama; Naoki Matsumoto, Yokohama; Kaichiro Kominato, Yamato; Hiroshi Tanaka, Chigasaki; Takeo Yoshioka, Ayase, all of Japan

[73] Assignee: Zaidan Hojin Biseibutsu Kagaku Kenkyukai, Tokyo, Japan

[21] Appl. No.: 256,537

[22] PCT Filed: Jan. 12, 1993

[86] PCT No.: PCT/JP93/00031

§ 371 Date: Jul. 13, 1994

§ 102(e) Date: Jul. 13, 1994

[87] PCT Pub. No.: WO93/14101

PCT Pub. Date: Jul. 22, 1993

[30] Foreign Application Priority Data

| Jan. 14, 1992 | [JP] | Japan | 4-24692 |
| Oct. 7, 1992 | [JP] | Japan | 4-268853 |
| Nov. 4, 1992 | [JP] | Japan | 4-295223 |
| Dec. 14, 1992 | [JP] | Japan | 4-332933 |

[51] Int. Cl.⁶ .................................................. C07H 17/08
[52] U.S. Cl. .................................................... 536/7.1
[58] Field of Search ............................ 536/7.1; 514/30; 424/180

[56] References Cited

U.S. PATENT DOCUMENTS

| 4,438,109 | 3/1984 | Umezawa et al. | 514/30 |
| 5,096,888 | 3/1992 | Umezawa et al. | 424/180 |

FOREIGN PATENT DOCUMENTS

| 104028 | 3/1984 | European Pat. Off. . |
| 124216 | 11/1984 | European Pat. Off. . |
| 132895 | 2/1985 | European Pat. Off. . |
| 154495 | 9/1985 | European Pat. Off. . |
| 0347158 | 12/1989 | European Pat. Off. . |
| 490311 | 6/1992 | European Pat. Off. . |
| 57-28100 | 2/1982 | Japan . |
| 57-42698 | 3/1982 | Japan . |
| 2191295 | 7/1990 | Japan . |
| 2275894 | 11/1990 | Japan . |
| 3184991 | 8/1991 | Japan . |
| 2081711 | 2/1982 | United Kingdom . |

OTHER PUBLICATIONS

Kageyama et al "Synthesis of 3,4'-Dideoxymycaminogyl Tylonoxide, a Novel Type of Macrolide Derivative", The Journal of Antibiotics, Jan., 1992, pp. 144-146.

*Primary Examiner*—Nathan M. Nutter
*Attorney, Agent, or Firm*—Cushman Darby & Cushman

[57] ABSTRACT

A compound of the following formula is provided:

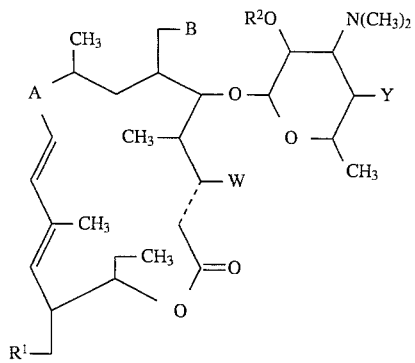

wherein A represents a carbonyl group which may be protected; B represents an aldehyde group which may be protected; $R^1$ represents a hydroxyl group which may be protected; $R^2$ represents a hydrogen atom or acyl group; W represents a hydrogen atom, hydroxyl group, lower alkanoyloxy group or substituted sulfonyloxy group; Y represents a hydrogen atom, halogen atom, hydroxyl group or substituted sulfonyloxy group; and broken line "------" represents a double bond or single bond. This compound is useful for producing 3,4'-dideoxymycaminosyltylonolide useful as an antimicrobial agent.

10 Claims, No Drawings

3,4'-DIDEOXYMYCAMINOSLTYLONOLIDE DERIVATIVE AND PROCESS FOR PRODUCING THE SAME

TECHNICAL FIELD

The present invention relates to an intermediate useful for producing 3,4'-dideoxymycaminosyltylonolide which is an antimicrobial substance having an excellent effect of protection from an infection, and a process for producing the same.

BACKGROUND ART 3,4'-Dideoxymycaminosyltylonolide and salts thereof exhibit an antimicrobial activity on Gram-positive and Gram-negative microorganisms, and they are usable as antimicrobial agents having particularly excellent effect of protection from an infection [see Japanese Patent Unexamined Published Application (hereinafter referred to as "J. P. KOKAI") No. Hei 2-275894].

3,4'-Dideoxymycaminosyltylonolide can be produced by protecting functional groups of mycaminosyltylonolide which is an acid hydrolyzate of tylosin, then converting the hydroxyl groups at the 3-position and 4'-position into deoxy groups and further removing the protecting groups. For converting the hydroxyl group at the 4'-position into deoxy group, a known process can be employed, such as a process wherein the hydroxyl groups at the 3-position and 4'-position are sulfonylated, then the hydroxyl group at the 4' position is halogenated by a method described in J. Antibiotics 34, pages 1374 to 1376 or J. P. KOKAI No. Hei 2-191295 and the halogen atom is removed by reduction with tributyltin hydride. The sulfonic acid can be eliminated from the hydroxyl group at the 3-position to form a double bond, which is catalytically reduced to form the deoxy compound.

However, the above-described process for producing 3,4'-dideoxymycaminosyltylonolide has a defect in that the yield of the intended product is low, since the conversion of the hydroxy groups at the 3-position and 4'-position into deoxy group necessitates the following steps: sulfonylating both hydroxyl groups; halogenating the hydroxyl group at the 4'-position and removing the halogen atom by reduction with tributyltin hydride; and forming double bond elimitating sulfonyloxy group at the 3-position and reducing the double bond. In addition, tributyltin hydride used for forming the deoxy group at the 4'-position has an offensive odor to make the purification of the reaction product difficult. Thus problems are posed when this reaction is employed on an industrial scale.

Therefore, the object of the present invention is to provide a useful intermediate for producing 3,4'-dideoxymycaminosyltylonolide. Another object of the present invention is to provide a process for efficiently converting the groups at the 3- and 4'-positions into deoxy group.

DISCLOSURE OF THE INVENTION

As a useful intermediate for producing 3,4'-dideoxymycaminosyltylonolide, the present invention provides a compound of the following formula (I):

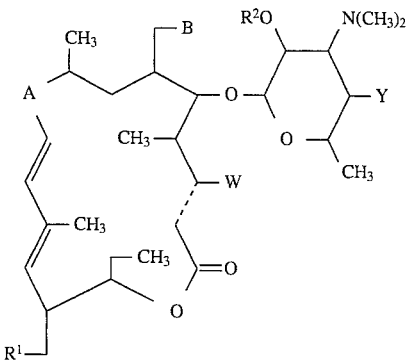

wherein A represents a carbonyl group which may be protected; B represents an aldehyde group which may be protected; $R^x$ represents a hydroxyl group which may be protected; $R^2$ represents a hydrogen atom or acyl group; W represents a hydrogen atom, hydroxyl group, lower alkanoyloxy group or substituted sulfonyloxy group; Y represents a hydrogen atom, halogen atom, hydroxyl group or substituted sulfonyloxy group; and broken line "-------" represents a double bond or single bond.

Examples of the compounds of the present invention represented by the formula (I) include the following ones:

(a) compounds of the formula (I) wherein A, B and $R^2$ are as defined above, $R^1$ represents a group Of the following formula:

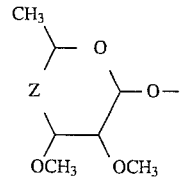

(Z being $CHR^4$ or C=O, and $R^4$ being a hydroxyl group which may be protected), W represents a hydrogen atom or substituted sulfonyloxy group, Y represents a hydrogen atom, halogen atom or substituted sulfonyloxy group, and broken line "-------" represents a single bond;

(b) compounds of the formula (I) wherein A, B and $R^2$ are as defined above, $R^1$ represents a group of the following formula:

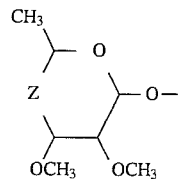

(Z being $CHR^4$ or C=O, and $R^4$ being a hydroxyl group which may be protected), W represents a hydrogen atom or lower alkanoyloxy group, Y represents a halogen atom, hydroxyl group or substituted sulfonyloxy group, and broken line "-------" represents a double bond when W is hydrogen atom and a single bond when W is a lower alkanoyloxy group; and (c) compounds of the formula (I) wherein A, B and $R^2$ are as defined above, $R^1$ represents a hydroxyl group which may be protected [with the proviso that $R^1$ cannot be a group of the following formula:

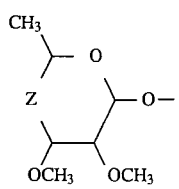

(Z being CHR⁴ or C=O, and $R^4$ being a hydroxyl group which may be protected)], W represents a hydrogen atom or lower alkanoyloxy group, Y represents a halogen atom, hydroxyl group or substituted sulfonyloxy group, and broken line "-------" represents a double bond when W is hydrogen atom and a single bond when W is a lower alkanoyloxy group.

In another embodiment, the present invention provides:

(d) a process for producing a compound 6f the formula (I) wherein A, B, $R^1$ and $R^2$ are as defined above, W and Y each represent a hydrogen atom and broken line "-------" represents a single bond by reducing a compound of the formula (I) wherein A, B, $R^1$ and $R^2$ are as defined above, W represents a substituted sulfonyloxy group, Y represents a halogen atom and broken line "-------" represents a single bond under an alkaline condition, and (e) a process for producing a compound of the formula (I), which comprises steps of reacting a compound of the formula (I) wherein A, B, $R^1$ and $R^2$ are as defined above, W and Y each represent a hydroxyl group and broken line "-------" represents a single bond with a sulfonylating agent to form a compound of the above formula (I) wherein A, B, $R^1$ and $R^2$ are as defined above, W and Y each represent a substituted sulfonyloxy group and broken line "-------" represents a single bond; reacting the resultant compound with a halogenating agent to form a compound of the formula (I) wherein A, B, $R^1$ and $R^2$ are as defined above, W represents a substituted sulfonyloxy group, Y represents a halogen atom and broken line "-------" represents a single bond; and reducing the resultant compound under an alkaline condition to form a compound of the formula (I) wherein A, B, $R^1$ and $R^2$ are as defined above, W and Y each represent a hydrogen atom and broken line "-------" represents a single bond.

BEST MODE FOR CARRYING OUT THE INVENTION

In the formula (I) for the compound of the present invention, A represents a carbonyl group which may be protected, and B represents an aldehyde group which may be protected. The protecting group for the carbonyl and aldehyde groups may be any of those well known in the art. They include, for example, acetals (or thioacetals) and ketals (or thioketals) which may contain substituents such as methyl group; e.g. dimethylacetal (dimethylketal), diethylacetal (diethylketal), diethylthioacetal (diethylthioketal), ethyleneacetal (ethyleneketal) and propyleneacetal (propyleneketal).

In the formula (I) of the compound of the present invention, $R^1$ represents a hydroxyl group which may be protected. The protecting group for the hydroxyl group may be any of those well known in the art. They include, for example, alkylsilyl groups such as t-butyldimethylsilyl, dimethylhexylsilyl, trimethylsilyl, triethylsilyl and tri(t-butyl)silyl groups; trityl group; tetrahydropyranyl group; tetrahydrofuranyl group; allyl group; lower alkanoyl groups such as substituted and unsubstituted acetyl groups; benzoyl group; benzyl group; methoxymethyl group; and benzyloxycarbonyl group. The substituted acetyl groups include, for example, halogen-substituted acetyl groups such as fluoroacetyl, difluoroacetyl, trifluoroacetyl, chloroacetyl, dichloroacetyl, trichloroacetyl, bromoacetyl and dibromoacetyl groups; and alkoxyacetyl groups such as methoxyacetyl, ethoxyacetyl and phenoxyacetyl groups. Mycinosyl group is also usable as the protecting group for the hydroxyl group. The hydroxyl group of mycinosyl group may be protected with a protecting group listed above for the hydroxyl group.

In the formula (I) for the compound of the present invention, $R^2$ represents a hydrogen atom or acyl group. The acyl groups include, for example, lower alkanoyl groups, lower alkenoyl groups, aroyl groups and phenyl(lower)alkanoyl groups. The lower alkanoyl groups include, for example, linear or branched alkanoyl groups having 1 to 6 carbon atoms. They include acyl groups such as formyl, acetyl, propionyl, butyryl, isobutyryl, valeryl, isovaleryl, pivaloyl and hexanoyl groups; aroyl groups such as benzoyl, toluoyl and xyloyl groups; and phenyl(lower) alkanoyl groups such as phenylacetyl, phenylpropionyl and phenylhexanoyl groups.

In the formula (I) for the compound of the present invention, W represents a hydrogen atom, hydroxyl group, lower alkanoyloxy group or substituted sulfonyloxy group. The lower alkanoyloxy groups include, for example, linear or branched alkanoyloxy groups having 1 to 6 carbon atoms. In particular, the alkanoyloxy groups include acetoxy and propionyloxy groups, etc. The substituted sulfonyloxy group is represented by the formula: —OSO₂R₃ wherein $R^3$ represents, for example, a lower alkyl group, trifluoromethyl group, 2-oxo-10-bornanyl group, substituted or unsubstituted aryl group or substituted or unsubstituted aralkyl group. The lower alkyl groups include, for example, methyl, ethyl, propyl, isopropyl, butyl, isobutyl, tert-butyl, pentyl, 1-methylbutyl, 2-methylbutyl and neopentyl groups. The substituted or unsubstituted aryl groups include, for example, phenyl, p-methoxyphenyl, p-nitrophenyl, p-fluorophenyl, o,p-difluorophenyl, p-chlorophenyl, m-chlorophenyl, o-chlorophenyl, o,p-dichlorophenyl, p-bromophenyl, p-methylphenyl, m-methylphenyl, o,p-dimethylphenyl, m,p-dimethylphenyl and naphthyl groups. The substituted or unsubstituted aralkyl groups include, for example, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl and p-fluorobenzyl groups.

In the formula (I) for the compound of the present invention, Y represents a hydrogen atom, halogen atom, hydroxyl group or substituted sulfonyloxy group. The halogen atom may be any of chlorine, bromine and iodine atoms. The substituted sulfonyloxy groups are those described above. When Y represents a halogen atom, hydroxyl group or substituted sulfonyloxy group, the configuration of the substituent Y is such that it is at either cis- or trans-position to the adjacent dimethylamino group [—N(CH₃)₂]. Therefore, the compound of the general formula (I) include a geometrical isomer in which the configuration of the substituent Y is such that it is at either cis- or trans-position to the adjacent dimethylamino group [—N(CH₃)₂] or a mixture of the isomers in any proportion. The broken line "-------" represents a double bond or a single bond.

A preferred embodiment of the present invention is a compound (a) of the formula (I) wherein A, B and $R^2$ are as defined above, $R^1$ represents a group of the following formula:

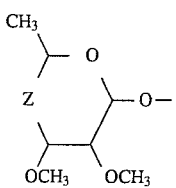

(Z being CHR$^4$ or C=O, and R$^4$ being a hydroxyl group which may be protected), W represents a hydrogen atom or substituted sulfonyloxy group, Y represents a hydrogen atom, halogen atom or substituted sulfonyloxy group, and broken line "------" represents a single bond;

Another preferred embodiment of the present invention is a compound (b) of the formula (I) wherein A, B and R$^2$ are as defined above, R$^1$ represents a group of the following formula:

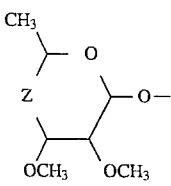

(Z being CHR$^4$ or C=O, and R$^4$ being a hydroxyl group which may be protected), W represents a hydrogen atom or lower alkanoyloxy group, Y represents a halogen atom, hydroxyl group or substituted sulfonyloxy group, and broken line "------" represents a double bond when W is hydrogen atom and a single bond when W is a lower alkanoyloxy group.

Furthermore, another preferred embodiment of the present invention is a compound (c) of the formula (I) wherein A, B and R$^2$ are as defined above, R$^1$ represents a hydroxyl group which may be protected [with the proviso that R$^1$ cannot be a group of the following formula:

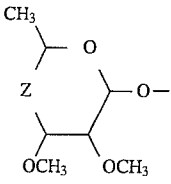

(Z being CHR$^4$ or C=O, and R$^4$ being a hydroxyl group which may be protected)], W represents a hydrogen atom or lower alkanoyloxy group, Y represents a halogen atom, hydroxyl group or substituted sulfonyloxy group, and broken line "------" represents a double bond when W is hydrogen atom and a single bond when W is a lower alkanoyloxy group.

In the above-described compounds (a), (b) and (c), Z represents CHR$^4$ or C=O, and R$^4$ represents a hydroxyl group which may be protected. The hydroxyl group which may be protected may be selected from among the above-mentioned ones excluding hydroxyl group protected with mycinosyl group.

The compounds of the present invention can be produced by, for example, a scheme which will be given below. However, the compounds of the present invention and the processes for producing them are not limited to the compounds and processes described in the schemes. The numbers of the compounds in the schemes correspond to Examples given in this specification.

Abbreviation:
Ac: acetyl
Bes: benzylsulfonyl
DM: desmycosin
DMT: demycinosyltylosin
Do: deoxy
ED: ethylenedioxy
iVal: isovaleryl
Ms: methanesulfonyl
MT: mycaminosyltylonolide
TBDS: t-butyldimethylsilyl
TMS: trimethylsilyl
EDMT: mycaminosyltylonolide 9,20-bis(ethyleneacetal)
TBDS-EDMT: 23-O-t-butyldimethylsilylmycaminosyltylonolide 9,20-bis(ethyleneacetal)
3,4'-Bes-TBDS-EDMT: 3,4'-di-O-benzylsulfonyl-23-O-t-butyldimethylsilylmycaminosyltylonolide 9,20-bis(ethyleneacetal)
3-Bes-4'-I-TBDS-EDMT: 3-O-benzylsulfonyl-23-O-t-butyldimethylsilyl-4'-deoxy-4'-iodomycaminosyltylonolide 9,20-bis(ethyleneacetal)
3,4'-Do-TBDS-EDMT: 23-O-t-butyldimethylsilyl-3,4'-dideoxymycaminosyltylonolide 9,20-bis(ethyleneacetal)
3,4'-Do-MT: 3,4'-dideoxymycaminosyltylonolide
2'-Ac-EDDM: 2'-O-acetyl desmycosin 9,20-bis(ethyleneacetal)
2'-Ac-4"-TMS-EDDM: 2'-O-acetyl-4"-O-trimethylsilyl desmycosin 9,20-bis(ethyleneacetal),
2',4"-Ac-EDDM: 2',4"-di-O-acetyl desmycosin 9,20-bis(ethyleneacetal),
2'-Ac-3,4'-Ms-4"-TMS-EDDM: 2'-O-acetyl-3,4'-di-O-methanesulfonyl-4"-O-trimethylsilyl desmycosin 9,20-bis(ethyleneacetal),
2'-Ac-4'-I-3Ms-4"-TMS-EDDM: 2'-O-acetyl-4'-deoxy-4'-iodo-3-O-methanesulfonyl -4"-O-trimethylsilyl desmycosin 9,20-bis(ethyleneacetal),
3,4'-Do-EDDM: 3,4'-dideoxy desmycosin 9,20-bis(ethyleneacetal),
2'-Ac-3,4'-Do-EDDM: 2'-O-acetyl-3,4'-dideoxy desmycosin 9,20-bis(ethyleneacetal),
2'-Ac-3,4'-Do-4"-Oxo-EDDM: 2'-O-acetyl-3,4'-dideoxy-4"-oxo desmycosin 9,20-bis(ethyleneacetal),
3,4'-Do-EDMT: 3,4'-dideoxymycaminosyltylonolide 9,20-bis(ethyleneacetal),
3,2',4"-Ac-EDDM: 3,2',4"-tri-O-acetyl desmycosin 9,20-bis(ethyleneacetal),
2',4"-Ac-Δ$^2$-EDDM: 2',4"-di-O-acetyl-2,3-dehydro-3-deox y desmycosin 9,20-bis(ethyleneacetal),
2',4"-Ac-Δ$^2$-4'-Ms-EDDM: 2',4"-di-O-acetyl-2,3-dehydro-3-deoxy-4' -O-methanesulfonyl desmycosin 9,20-bis(ethyleneacetal),
2',4"-Ac-Δ$^2$-4'-I-EDDM: 2',4"-O-acetyl-2,3-dehydro-3,4'-dideoxy-4'-iodo desmycosin 9,20-bis(ethyleneacetal),
3,2',4"-Ac-4'-Ms-EDDM: 3,2',4"-tri-O-acetyl-4'-O-methanesulfonyl desmycosin 9,20-bis(ethyleneacetal),
3,2',4"-Ac-4'-I-EDDM: 3,2',4"-tri-O-acetyl-4'-deoxy-4'-iodo desmycosin 9,20-bis(ethyleneacetal),
3,2'-Ac-4"-iVal-DMT: 3,2'-di-O-acetyl-4"-O-isovaleryldeemycinosyltylosin, 3,2'-Ac-MT: 3,2'-di-O-acetylmycaminosyltylonolide, 3,2'-Ac-EDMT: 3,2'-di-O-acetylmycaminosyltylonolide 9,20-bis(ethyleneacetal)

3,2'-Ac-TBDS-EDMT: 3,2'-di-O-acetyl-23-O-t-butyldimethylsilylmycaminosyltylonolide 9,20-bis(ethyleneacetal)

2'-Ac-Δ²-TBDS-EDMT: 2-O-acetyl-23-O-t-butyldimethylsilyl-2, 3-dehydro-3-deoxymycaminosyltylonolide, 9,20-bis(ethyleneacetal)

2'-Ac-Δ²-4'-Ms-TBDS-EDMT: 2'-O-acetyl-23-O-t-butyldimethylsilyl-2,3-dehydro -3-deoxy-4'-O-methanesulfonylmycaminosyltylonolide 9,20-bis(ethyleneacetal)

2'-Ac-Δ²-4'-I-TBDS-EDMT: 2'-O-acetyl-23-O-t-butyldimethylsilyl-2,3-dehydro -3,4'-dideoxy-4'-iodomycaminosyltylonolide 9,20-bis(ethyleneacetal)

3,2'-Ac-4'-Ms-TBDS-EDMT: 3,2'-di-O-acetyl-23-O-t-butyldimethylsilyl-4'-O-methanesulfonylmycaminosyltylonolide 9,20-bis(ethyleneacetal), and 3,2'-Ac-4'-I-TBDS-EDMT: 3,2'-di-O-acetyl-23-O-t-butyldimethylsilyl-3,4'-dideoxy-4'-iodomycaminosyltylonolide 9,20bis(ethyleneacetal).

Production Scheme 1 tylosin → MT → EDMT → TBDS-EDMT →

-continued
Production Scheme 1
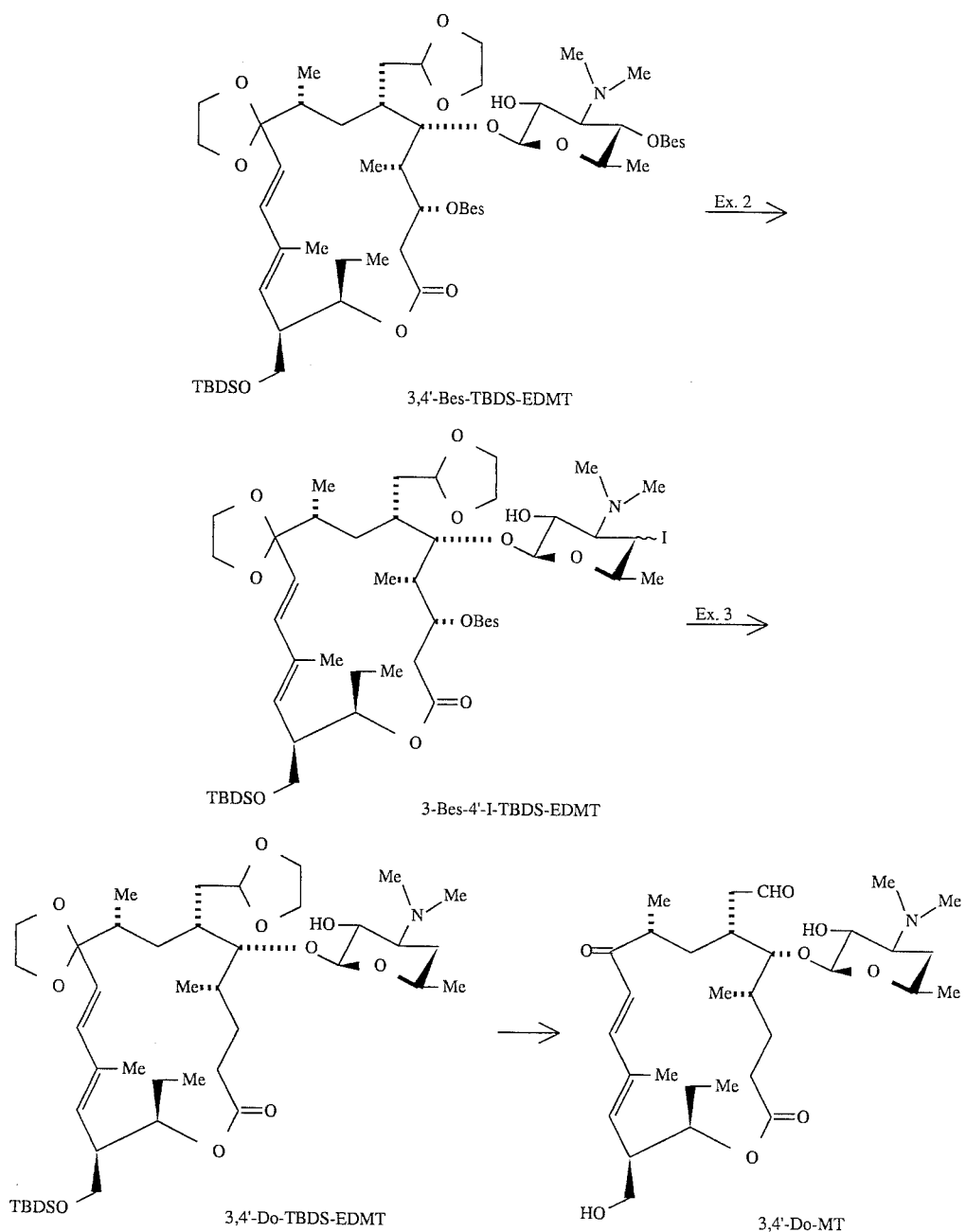

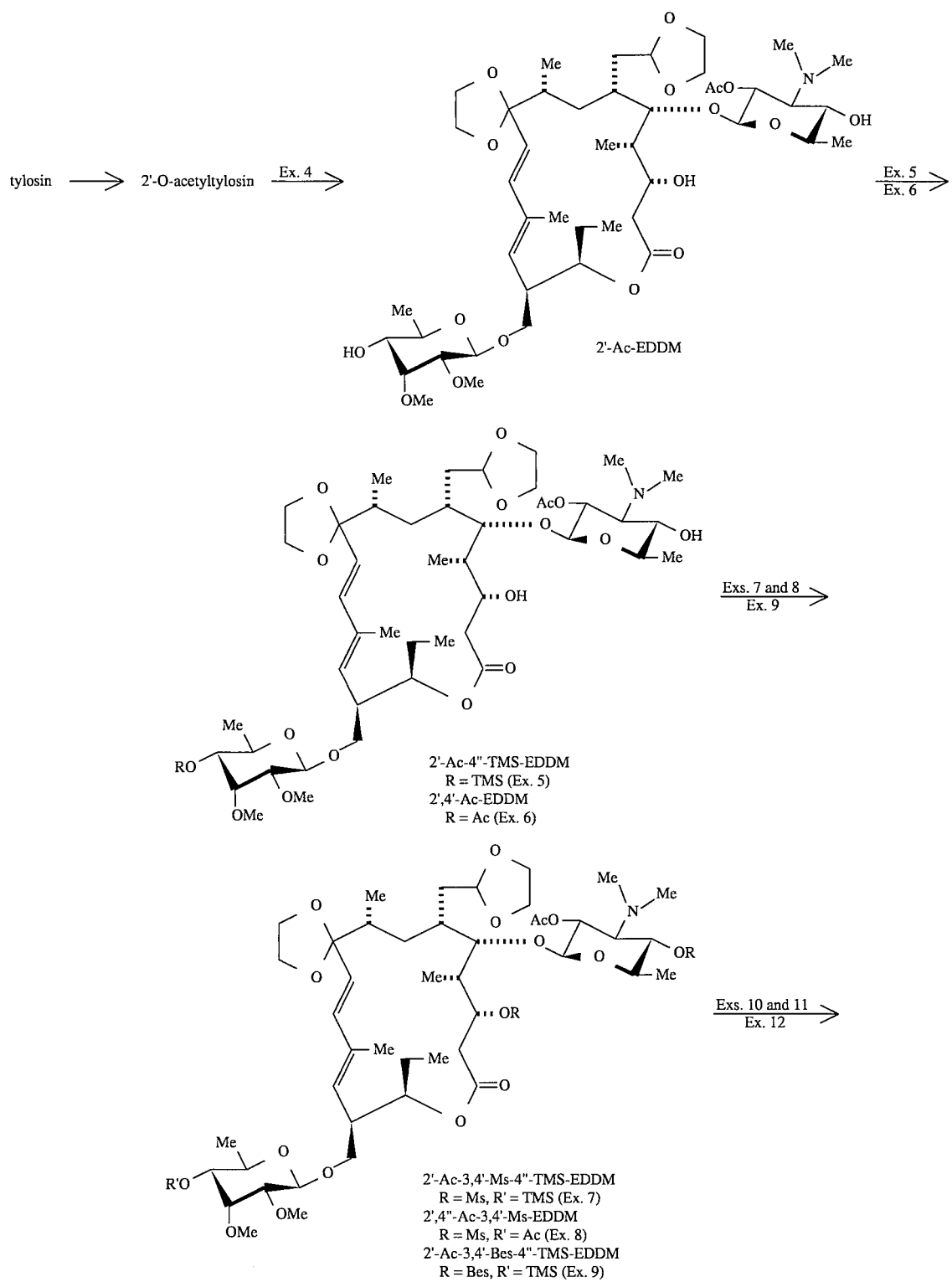

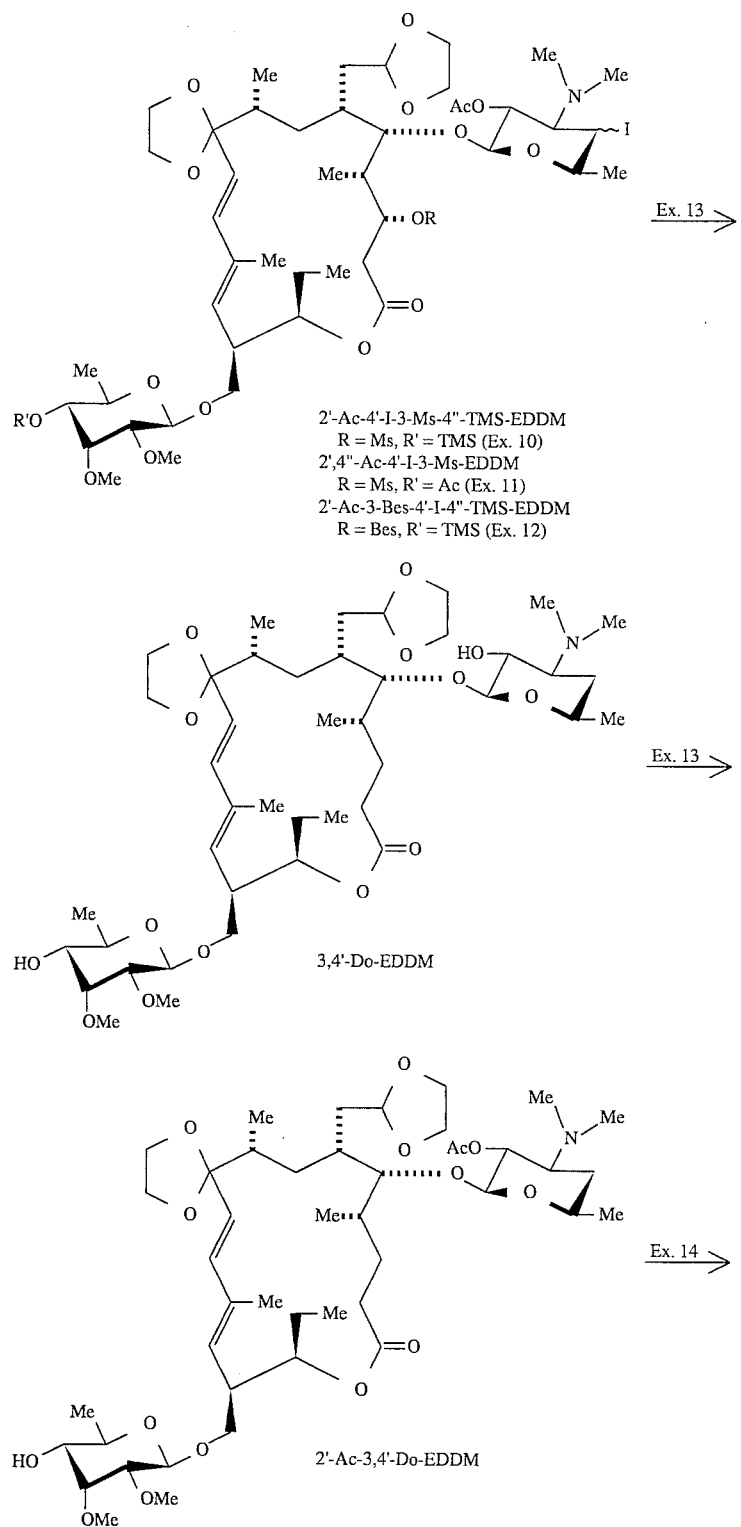

-continued
Production scheme 2
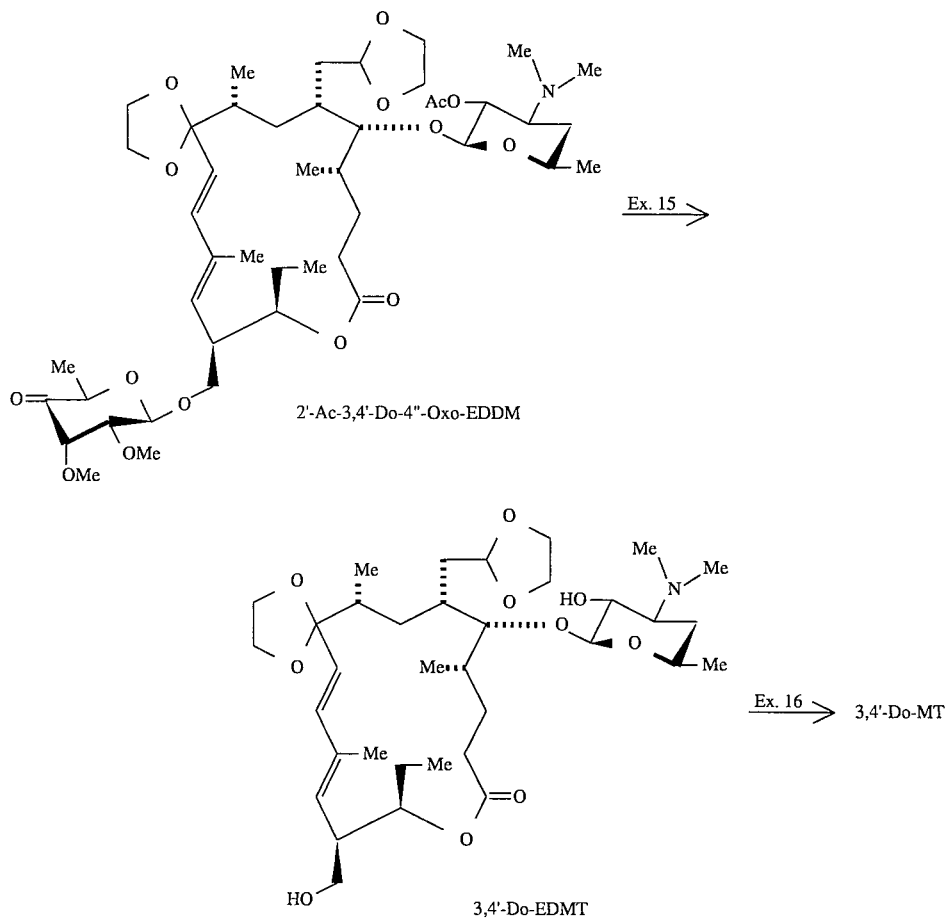
2'-Ac-3,4'-Do-4''-Oxo-EDDM
Ex. 15 →
3,4'-Do-EDMT
Ex. 16 → 3,4'-Do-MT
Production scheme 3-1
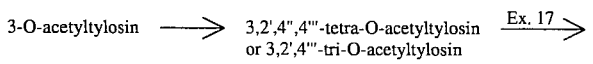
3-O-acetyltylosin ⟶ 3,2',4'',4'''-tetra-O-acetyltylosin or 3,2',4'''-tri-O-acetyltylosin  Ex. 17 →
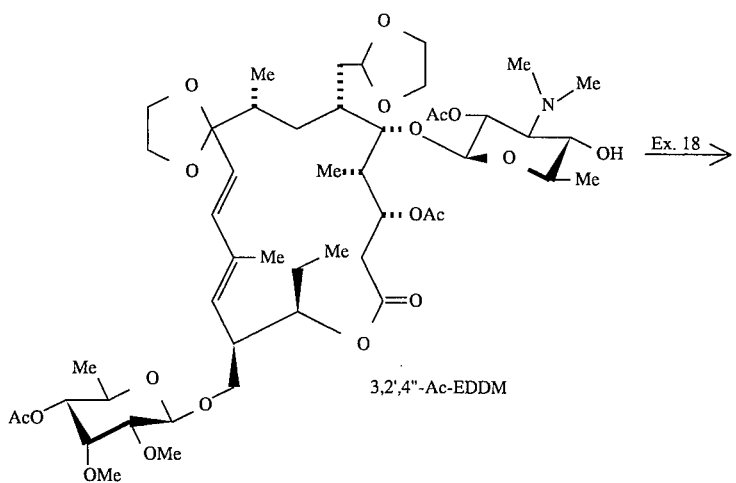
3,2',4''-Ac-EDDM
Ex. 18 →

-continued
Production scheme 3-1
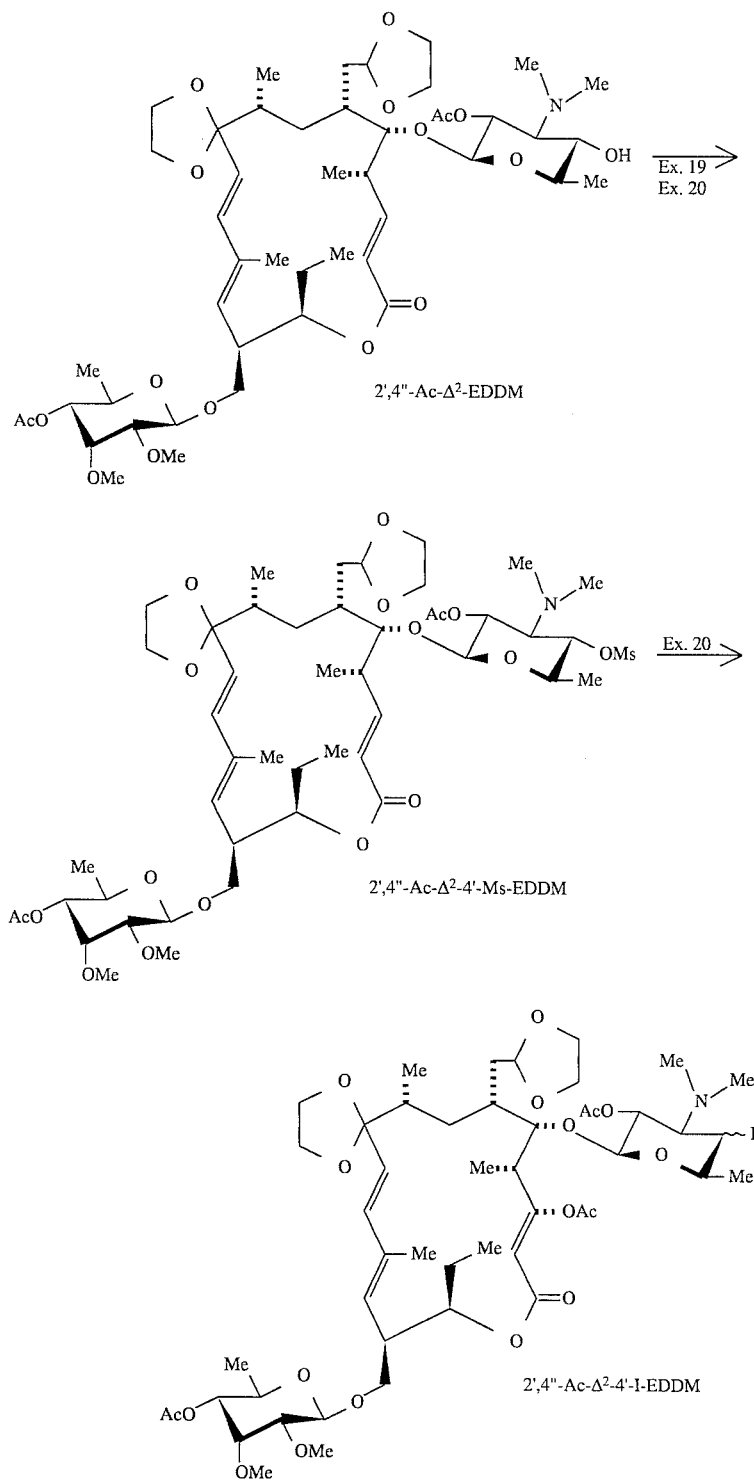

Production scheme 3-2
3,2',4"-Ac-EDDM $\xrightarrow[\text{Ex. 22}]{\text{Ex. 21}}$
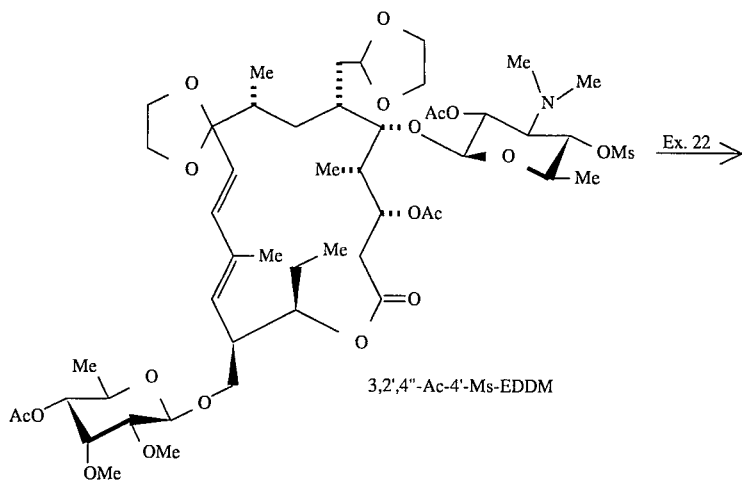
3,2',4"-Ac-4'-Ms-EDDM $\xrightarrow{\text{Ex. 22}}$
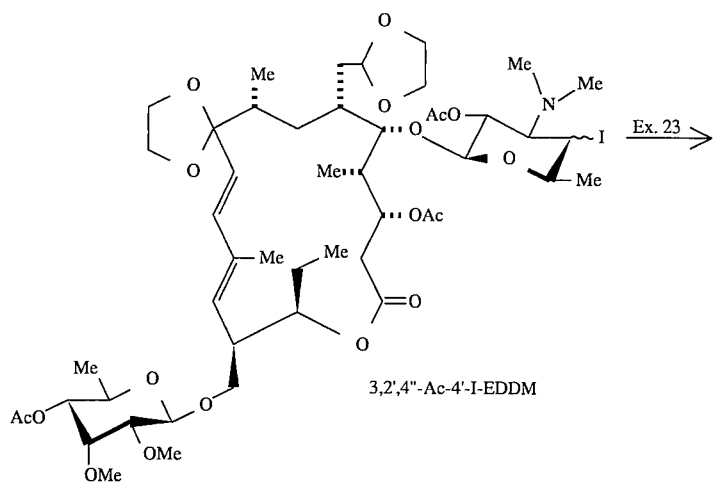
3,2',4"-Ac-4'-I-EDDM $\xrightarrow{\text{Ex. 23}}$
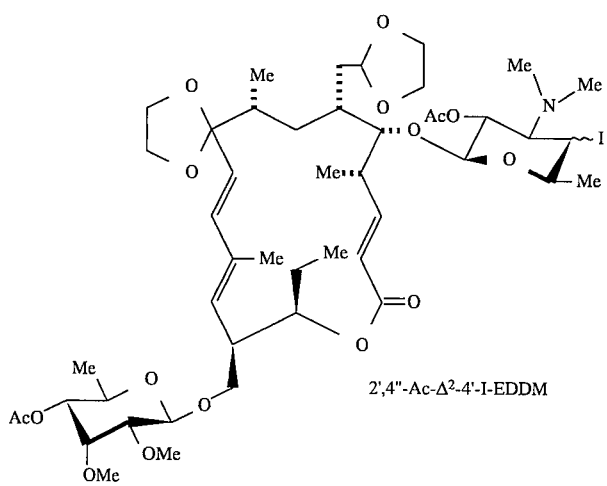
2',4"-Ac-$\Delta^2$-4'-I-EDDM Production scheme 3-3
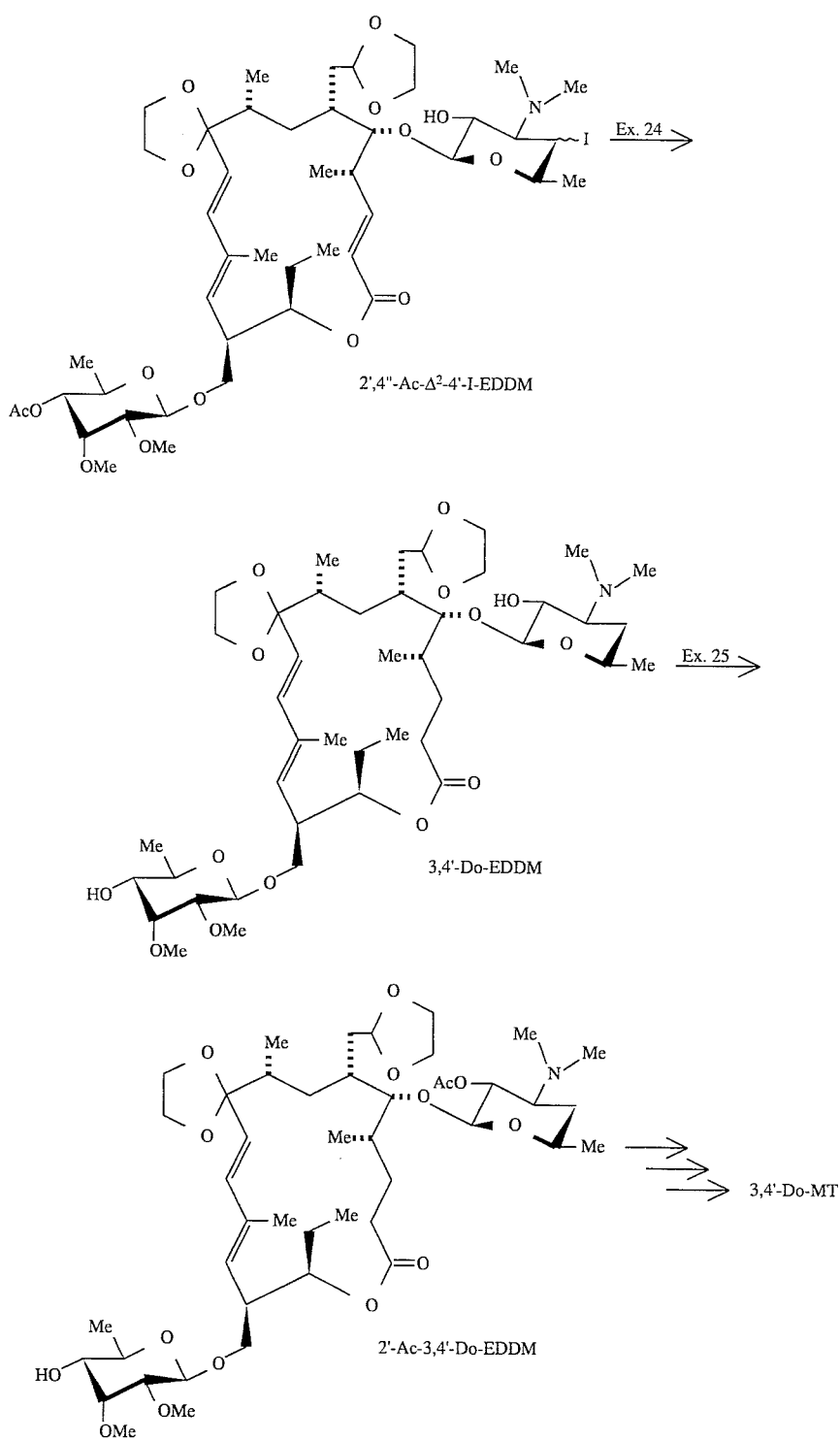

Production Scheme 4-1
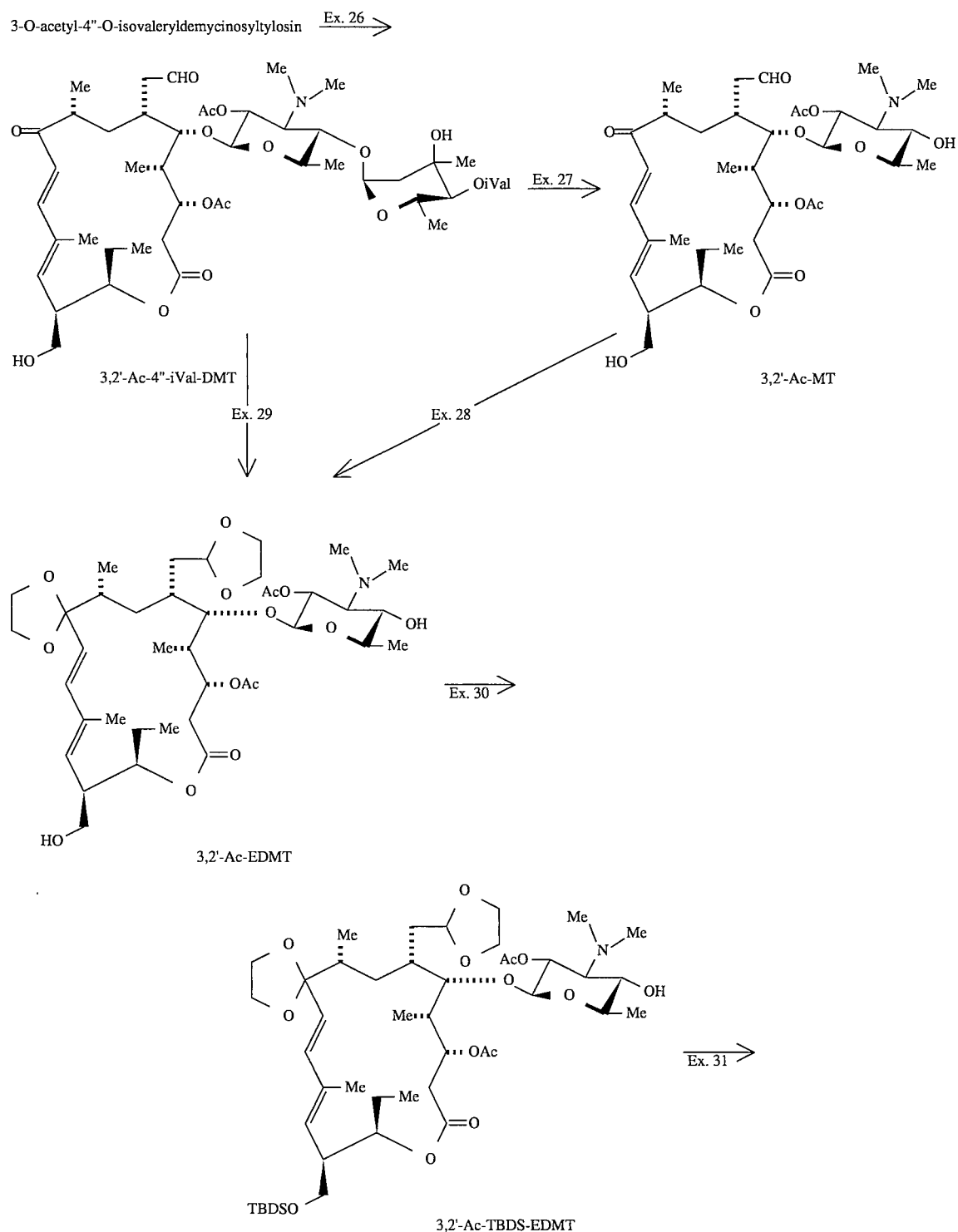

-continued
Production Scheme 4-1
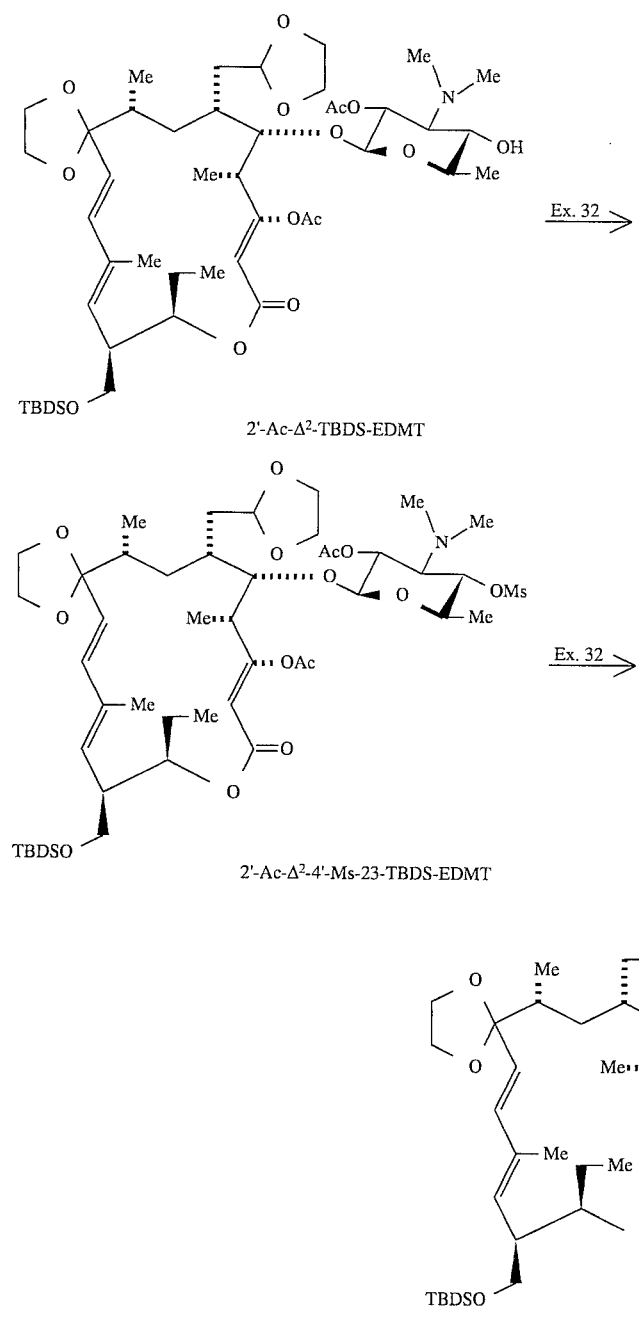

Production Scheme 4-2
3,2'-Ac-TBDS-EDMT $\xrightarrow[\text{Ex. 34}]{\text{Ex. 33}}$
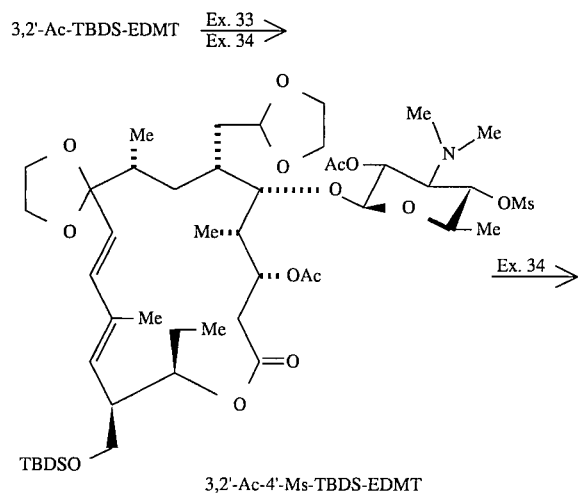
3,2'-Ac-4'-Ms-TBDS-EDMT
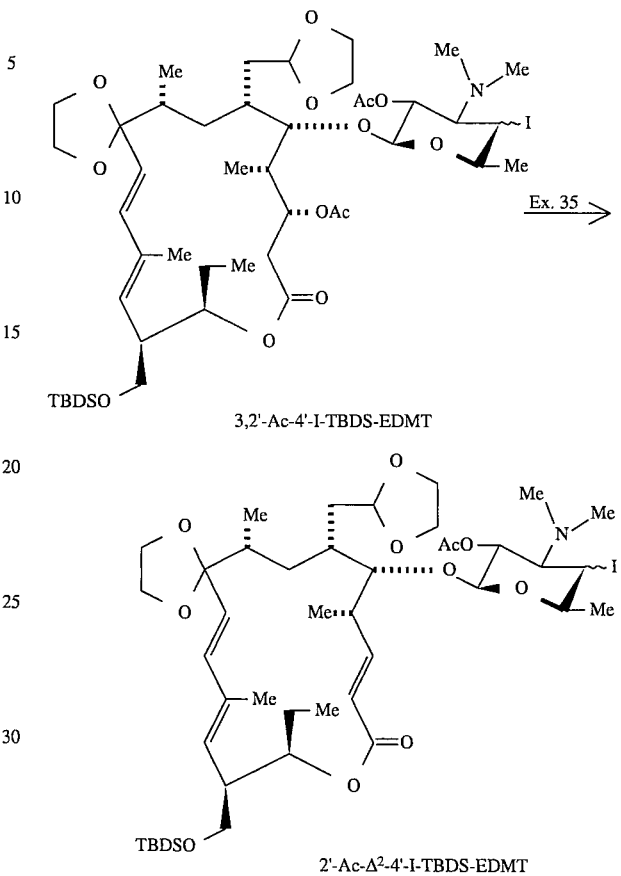
3,2'-Ac-4'-I-TBDS-EDMT
2'-Ac-Δ²-4'-I-TBDS-EDMT
Production scheme 4-3
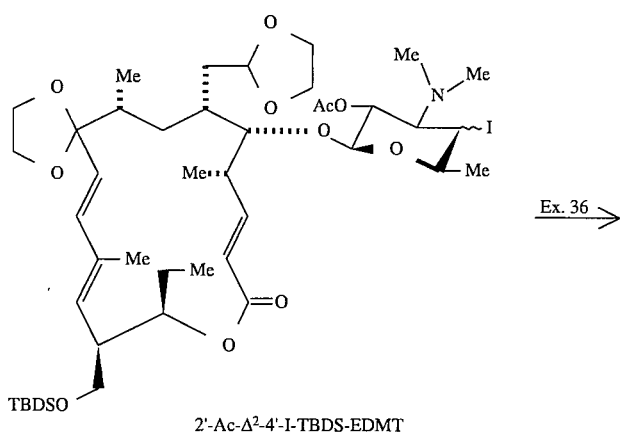
2'-Ac-Δ²-4'-I-TBDS-EDMT -continued
Production scheme 4-3

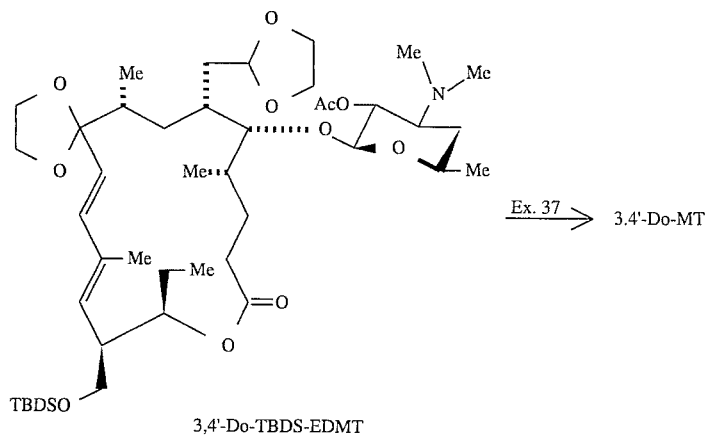

3,4'-Do-TBDS-EDMT    Ex. 37 → 3.4'-Do-MT

The present invention provides:

(d) a process for producing a compound of the above formula (I) wherein A, B, R¹ and R² are as defined above, W and Y each represent a hydrogen atom and the broken line "-------" represents a single bond by reducing a compound of the formula (I) wherein A, B, R¹ and R² are as defined above, W represents a substituted sulfonyloxy group, Y represents a halogen atom and the broken line "-------" represents a single bond under an alkaline condition; and (e) a process for producing a compound of the above formula (I) wherein A, B, R¹ and R² are as defined above, W and Y each represent a hydrogen atom and the broken line "-------" represents a single bond, which comprises steps of reacting a compound of the formula (I) wherein A, B, R¹ and R² are as defined above, W and Y each represent a hydroxyl group and the broken line "-------" represents a single bond with a sulfonylating agent to form a compound of the above formula (I) wherein A, B, R¹ and R² are as defined above, W and Y each represent a substituted sulfonyloxy group and the broken line "-------" represents a single bond; reacting the compound thus obtained with a halogenating agent to form a compound of the above formula (I) wherein A, B, R¹ and R² are as defined above, W represents a substituted sulfonyloxy group, Y represents a halogen atom and the broken line "-------" represents a single bond; and reducing the compound thus obtained under an alkaline condition to obtain a compound of the above formula (I) wherein A, B, R¹ and R² are as defined above, W and Y each represent a hydrogen atom and the broken line "-------" represents a single bond.

The compounds of the above-mentioned formula wherein A, B, R¹ and R² are as defined above, W and Y each represent a hydrogen atom and the broken line "-------" represents a single bond, thus produced by the above-described processes, are also preferred ones in the present invention.

The mycaminosyltylonolide derivatives shown in the above production schemes 1 and 2 can be produced from easily available tylosin. For example, they can be produced by hydrolyzing tylosin with an acid and then protecting, if necessary, hydroxyl, aldehyde and carbonyl groups of the obtained mycaminosyltylonolide with the abovedescribed protecting group. Another process is disclosed in Journal of Antibiotics (35, 661, 1982) wherein tylosin is treated with an acid anhydride to obtain 2'-o-acyltylosin, which is then hydrolyzed with an acid and simultaneously or therafter protected with the protecting group to obtain a mycaminosyltylonolide having a mycinosyl group.

By reacting the thus-obtained mycaminosyltylonolide derivative with a sulfonylating agent, the hydroxyl groups at the 3-position and 4'-position are converted into the substituted sulfonyloxy groups to form the corresponding compound. The sulfonylating agents are, for example, halides and anhydrides. The sulfonylating agent for giving a desired substituted sulfonyloxy group can be easily selected by those skilled in the art. Examples of the sulfonylating agents include methanesulfonyl chloride, methanesulfonic anhydride, ethanesulfonyl chloride, propanesulfonyl chloride, butanesulfonyl chloride, pentanesulfonyl chloride, trifluoromethanesulfonyl chloride, trifluoromethanesulfonic anhydride, benzenesulfonyl chloride, pmethoxyphenylsulfonyl chloride, p-nitrophenylsulfonyl chloride, p-fluorophenylsulfonyl chloride, o,p-difluorophenylsulfonyl chloride, p-chlorophenylsulfonyl fluorophenylsulfonylchloride, m-chlorophenylsulfonyl chloride, o-chlorophenylsulfonyl chloride, o,p-dichlorophenylsulfonyl chloride, p-bromophenylsulfonyl chloride, p-methylphenylsulfonyl chloride, p-methylphenylsuflonic anhydride, m-methylphenylsulfonyl chloride, o,p-dimethylphenylsulfonyl chloride, m,p-dimethylphenylsulfonyl chloride, naphthylsulfonyl chloride, camphorsulfonyl chloride, benzylsulfonyl chloride, p-nitrobenzylsulfonyl chloride, o,p-dinitrobenzylsulfonyl chloride, p-chlorobenzylsulfonyl chloride, m-chlorobenzylsulfonyl chloride, p-methylbenzylsulfonyl chloride, m-methylbenzylsulfonyl chloride, o-methylbenzylsulfonyl chloride, o,p-dimethylbenzylsulfonyl chloride, p-methoxybenzylsulfonyl chloride and p-fluorobenzylsulfonyl chloride. The sulfonylating agents are not limited to those listed above.

The sulfonylation reaction with the above-described sulfonylating agent is conducted usually in an organic solvent at a temperature ranging from −40° to +50° C. The solvents usable herein include, for example, acetonitrile, acetone, methyl ethyl ketone, dimethyl sulfoxide, dioxane and toluene. It is also possible to use pyridine, 4-dimethylaminopyridine, triethylamine or the like as the basic catalyst and/or solvent.

The compound produced by selectively introducing a halogen into the 4'-position can be obtained by reacting the mycaminosyltylonolide derivative in which the hydroxyl groups at the 3-position and 4'-position have been converted into the substituted sulfonyloxy group with a halogenating agent such as sodium iodide, potassium iodide, lithium bromide, tetrabutylammonium bromide or tetrabutylammonium chloride in an inert solvent such as acetone, methyl ethyl ketone, dimethoxyethane or dimethylformamide. The halogenation reaction is conducted usually at room temperature to 100° C. depending on the kind of the substituted sulfonyloxy group. Depending on the halogenation conditions, a compound having a double bond at 2- and 3-positions or at 3- and 4-positions is partially formed, which can be used as a starting compound in the subsequent step.

By reducing the above-described compound having the substituted sulfonyloxy group and halogen atom in place of the hydroxyl groups at the 3-position and 4'-position under the alkaline condition, the groups at the 3-position and 4'-position can be simultaneously replaced with hydrogen to form 3,4'-dideoxy derivative. This reaction can be conducted by, for example, a catalytic reduction in the presence of a catalyst in a solvent inert to the reaction. The bases usable for realizing the alkaline condition include, for example, sodium hydroxide, sodium carbonate, sodium hydrogencarbonate, potassium carbonate and potassium hydrogencarbonate. Among them, potassium carbonate is preferred. Such a base is used usually in an amount of 1 to 5 mol per mol of the 3-substituted sulfonyloxy-4'-halogen compound used as the substrate. The catalysts usable for the catalytic reduction include, for example, platinum, palladium and Raney nickel. Among them, Raney nickel is preferred. The amount of the catalyst which varies depending on the variety of the catalyst is usually ¹/₁₀ to ¹/₁ part by weight per part by weight of the compound used as the substrate. The inert solvents include, for example, methanol, ethanol and tetrahydrofuran. The catalytic reduction is conducted under cooling or at room temperature, preferably at a reaction temperature of $-10°$ to $+30°$ C. under a hydrogen pressure ranging from atmospheric pressure to 5 kg/cm$^2$. These conditions which vary depending on the starting compounds and the catalyst are suitably selected by those skilled in the art.

The groups at the 3-position and 4'-position of the 3-substituted sulfonyloxy-4'-halogen compound can be replaced with hydrogen at once by the above-described reaction. Thus, a high yield of 3,4'-deoxy compound can be obtained in one step. By removing the protecting groups from the 3,4'-deoxy compound by an ordinary method, it can be converted into 3,4'-dideoxymycaminosyltylonolide or a salt thereof useful as an antimicrobial agent. The protecting group can be removed usually by treatment with a mineral acid such as hydrochloric acid or sulfuric acid or with an organic acid such as acetic acid, trifluoroacetic acid or trichloroacetic acid in the presence of water. The protecting group can be removed also by treatment with an arylsulfonic acid such as p-toluenesulfonic acid or an alkylsulfonic acid such as methanesulfonic acid in a solvent such as dioxane, dimethylformamide, dimethyl sulfoxide or acetonitrile at room temperature or under heating. When the protecting group for the hydroxyl group is mycinosyl group, this group can be oxidized to form a corresponding ketone, which is then treated with an acid or base.

Compounds of the formula (I) of the present invention wherein A, B and R$^2$ are as defined above, W represents a hydrogen atom, Y represents a hydroxyl group, R$^1$ represents a protected hydroxyl group and the broken line "-------" represents a double bond (2',4"-di-O-acyl-Δ$^2$-desmycosin bisacetal) can be produced by the process of the above production scheme 3-1. By this process, 3-O-acetyltylosin easily available on the market (see Journal of Antibiotics 27, 542, 1979) is acylated to form 2',4'''-di- or 2',4",4'''-tri-O-acyl-3-O-acetyltylosin by, for example, a method described in Journal of Antibiotics 35, 661, 1982, then the resultant compound is treated with a dehydrating agent and an alcohol in the presence of about 1.1 to 1.5 mol, per mol of the compound, of an acid catalyst in an inert solvent such as toluene at a temperature of about 5° to 80° C. to form a 9,20-bisacetal of 2',4"-di-O-acyl-3-O-acetyl desmycosin, and finally the resultant compound is treated with about 1.0 to 5.0 mol, per mol of the compound, of a base in an inert solvent such as dimethyl sulfoxide.

The alcohols usable in the above-described reaction include, for example, methanol, ethanol, propanol, butanol, ethylene glycol, propanediol and 2,3-butanediol. Such an alcohol is used in an amount of about 5 to 20 mol, per mol of the starting compound. The dehydrating agents include, for example, ethyl orthoformate, methyl orthoformate, anhydrous calcium chloride, anhydrous sodium sulfate, anhydrous magnesium sulfate and molecular sieves. The acid catalysts include, for example. camphorsulfonic acid, benzenesulfonic acid, toluenesulfonic acid, methanesulfonic acid, sulfuric acid and Amberlyst 15. The bases usable in the acetic acid-removing step include, for example, sodium hydride, tert-butoxypotassium, magnesium methoxide, magnesium ethoxide, sodium methoxide, sodium ethoxide, 1,8-diazabicyclo[5.4.0]-7-undecene and 1,5-diazabicyclo[4.3.0]-5-nonene.

The above-described compound can be converted into a compound of the formula [I] wherein Y represents a substituted sulfonyloxy group by reacting it with the above-described sulfonylating agent in the presence of an organic base such as pyridine, collidine, lutidine, triethylamine or diisopropylethylamine in an inert solvent at a temperature of about $-25°$ to $+25°$ C. It is also possible to obtain a compound of the above formula [I] wherein Y represents a halogen atom by reacting the compound of the above formula [I] wherein Y represents a substituted sulfonyloxy group with about 1 to 5 mol, per mol of the compound, a halogenating agent in a solvent such as acetone, methyl ethyl ketone, dimethoxyethane, acetonitrile, dimethyl sulfoxide or dimethylformamide at a temperature of about 50° to 100° C.

The compound of the formula (I) of the present invention wherein A, B and R$^2$ are as defined above, W represents a hydrogen atom, Y represents a halogen atom, R$^1$ represents a protected hydroxyl group and the broken line "-------" represents a double bond can be converted into a corresponding 3,4'-deoxycompound by the hydrogen replacement at the 3-position and 4'-position at once by, for example, catalytic reduction under alkaline condition in the same manner as those described above. Then the protecting groups are removed by an ordinary method to obtain 3,4'-dideoxymycaminosyltylonolide or a salt thereof useful as the antimicrobial agent.

The compound of the present invention can be produced from 3-O-acetyltylosin according to, for example, the production scheme 3-2. For example, 3-O-acetyltylosin is acylated by a method described in Journal of Antibiotics (35, 661, 1982) to form 2',4'''-di- or 2',4",4'''-tri-O-acyl-3-O-acetyltylosin and then the resultant compound is converted into an acetal with a dehydrating agent, an alcohol and an acid catalyst to obtain 9,20-bisacetal of 2',4"-di-O-acyl-3-O-acetyl desmycosin.

In the acetalization reaction, an alcohol capable of forming an intended acetal or ketal is used either singly or in combination with an inert solvent. The alcohols include methanol, ethanol, propanol, butanol, ethylene glycolo, propanediol, 2,3-butanediol, etc. The alcohol is used in an amount of 5 to 20 mol per mol of the macrolide compound. The inert solvents usable herein include toluene, benzene, ethyl acetate, chloroform, dichloromethane, etc. The dehydrating agents include ethyl orthoformate as well as methyl orthoformate, anhydrous calcium chloride, anhydrous sodium sulfate, anhydrous magnesium sulfate, molecular sieves, etc. The acid catalysts include p-toluenesulfonic acid as well as benzenesulfonic acid, camphorsulfonic acid, methanesulfonic acid, sulfuric acid, Amberlyst 15, etc. The acid catalyst is preferably used in an amount of 1.1 to 1.5 mol per mol of the starting compound. The reaction temperature is 5° to 80° C., preferably 20° to 70° C. and particularly room temperature to 50° C.

The compound thus obtained can be converted into a compound sulfonylated at the 4'-position by reacting it with a sulfonylating agent under the above-described reaction conditions. The compound thus sulfonylated at the 4'-position is relatively unstable and, therefore, it is preferably subjected to the subsequent reaction without isolation or purification. This compound can be converted into a compound halogenated at the 4'-position by halogenation under the above-described conditions.

This compound can be converted into 2',4"-di-O-acyl-2,3-dehydro-3,4'-dideoxy-4'-halo-desmycosin bisacetal by removing acetic acid at the 2- and 3-positions as follows: the compound halogenated at the 4'-position is dissolved in an inert solvent such as toluene, diethyl ether, tetrahydrofuran, dimethoxyethane, dioxane, dimethyl sulfoxide or dimethylformamide, and then treated with a base such as sodium hydride, tert-butoxypotassium, maqnesium methoxide, magnesium ethoxide, sodium methoxide, sodium ethoxide, 1,8-diazabicyclo[5.4.0]-7-undecene or 1,5-diazabicyclo[4.3.0]-5-nonene. This reaction is conducted at, for example, a temperature of −10° to 80° C. The base is used in an amount of 1.0 to 5.0 mol, preferably 1.0 to 3.0 mol, per mol of the starting compound.

The compound thus obtained is dissolved in, for example, methanol or ethanol and catalytically reduced in the presence of a catalyst such as Raney nickel and a base under a hydrogen pressure ranging from atmospheric pressure to about 4.0 kg/cm$^2$ according to the production scheme 3—3 to obtain 3,4'-dideoxy desmycosin bisacetal. This reaction can be conducted at, for example, room temperature, and 1 to 3 mol of a base such as sodium hydrogencarbonate, potassium hydrogencarbonate, potassium carbonate or sodium carbonate is used per mol of the macrolide compound. When Raney nickel is used as the catalyst, the variety thereof is not particularly limited. For example, NDT-65 or NDHT-90 (a product of Kawaken Fine Chemicals, Co., Ltd.) is usable. It is preferred to conduct the reaction in the presence of 0.1 to 1.0 part by weight of the catalyst per part by weight of the macrolide compound. The resultant compounnd is treated with about 1.1 equivalent of an acid anhydride to introduce an acyl group into the 2'-position, thereby obtaining a corresponding 2'-O-acyl-3,4'-dideoxy desmycosin bisacetal.

This compund is treated with an oxidizing agent to oxidize the hydroxyl group at the 4"-position and to obtain a high yield of the intended compound. The oxidizing agents include, for example, combinations of dimethyl sulfoxide/ acetic anhydride, dimethyl sulfoxide/trifluoroacetic anhydride, dimethyl sulfoxide/dicyclohexylcarbodiimide/pyridine/trifluoroacetic acid, dimethyl sulfide/N-chlorosuccinimide/triethylamine and tetrahydrothiophene/ N-chlorosuccinimide/triethylamine as well as ordinary oxidizing agents having a secondary hydroxyl group. The oxidizing agent is used in an amount of about 2 to 10 mol per mol of the starting compound. Although the reaction conditions vary depending on the variety of the oxidizing agent, the reaction temperature ranges −20° C. to 80° C.

The mycinose part can be easily removed by treating the 4"-oxo compound obtained by the above-described process with a base in an inert solvent. For example, the 4"-oxo compound is treated with a base such as sodium hydroxide, potassium hydroxide, sodium carbonate, potassium carbonate, ammonium acetate, 1,8-diazabicyclo[5.4.0]-7-undecene or 1,5-diazabicyclo[4.3.0]-5-nonene in an organic solvent such as methanol, ethanol, dioxane, tetrahydrofuran, dimethoxyethane, dimethylformamide or a mixture of two or more of them or a mixture of such an organic solvent with water. Though the reaction temperature ranges from 0° to 100° C., a temperature below room temperature is preferred.

The acetyl group at the 2'-position can be removed by an alcoholysis reaction in a solvent such as methanol or ethanol prior to the mycinose-removing reaction or, alternatively, by the alcholysis reaction after the mycinose-removing reaction. 3,4'-dideoxymycaminosyltylonolide bisacetal thus obtained is dissolved in an organic solvent such as tetrahydrofuran or dioxane and then treated with dilute hydrochloric acid to conduct the deacetalization (deketalization), thereby obtaining 3,4'-dideoxymycaminosyltylonolide.

According to the production scheme 4-1, a 3-O-acetyl-4"-O-isovaleryldemycinosyltylosin (a compound described in J.P. KOKOKU No. Sho 60-16960) can be converted into a corresponding 2'-O-acyl-3-O-acetyl-4"-O -isovaleryldemycinosyltylosin by treating it with an acid anhydride selected from various ones as described in, for example, Journal of Antibiotics (35, 661, 1982). When the resultant compound is hydrolyzed under an acid condition realized in, for example, an aqueous solution of sulfuric acid, hydrochloric acid or phosphoric acid at −10° to 100° C., preferably 10° to 60° C., a corresponding 2'-O-acyl-3-O-acetylmycaminosyltylonolide is obtained. Further, this compound can be converted into 9,20-bisacetal of the 2'-O-acyl-3-O-acetylmycaminosyltylonolide by acetalizing it with a dehydrating agent, alcohol and acid catalyst under the above-described reaction conditions. On the other hand, when the 2'-O-acyl-3-O-acetyl-4"-O-isovaleryldemycinosyltylosin is subjected to the acetalization reaction under the above-described reaction conditions, acetalization and hydrolysis of the terminal saccharide occur at the same time to obtain 9,20-bisacetal of the 2'-O-acyl-3-O-acetylmycaminosyltylonolide in one step.

When 9,20-bisacetal of the 2'-O-acyl-3-O-acetylmycaminosyltylonolide thus obtained is reacted with, for example, a reactive silyl compound in the presence of a base, a corresponding compound having protected hydroxyl group at the 23-position can be obtained. The solvents usable for this reaction include dimethylformamide as well as acetone, acetonitrile, tetrahydrofuran, toluene and chloroform. The basic catalysts include inorganic and organic bases such as sodium carbonate, potassium carbonate, sodium hydrogencarbonate, pyridine, lutidine, picoline, triethylamine, diisopropylethylamine and imidazole. The reactive silyl compounds usable herein include trimethylsilyl chloride, triethylsilyl chloride, tripropylsilyl chloride, t-butyldimethylsilyl chloride, dimethoxymethylsilyl chloride, dimethylphenylsilyl chloride, etc. The reaction can be conducted at −10° to 50 ° C.

The compound having the protected hydroxyl group at the 23-position is dissolved in an inert solvent such as toluene, diethyl ether, tetrahydrofuran, dimethoxyethane, dioxane, dimethyl sulfoxide or dimethylformamide, and then reacted with a base such as sodium hydride, t-butoxypotassium, magnesium methoxide, magnesium ethoxide, sodium methoxide, sodium ethoxide, 1,8-diazabicyclo[5.4.0]-7-undecene or 1,5diazabicyclo[4.3.0]-5-nonene at −10° to 80° C. to obtain a corresponding 2'-O-acyl-2,3-dehydro-mycaminosyltylonolide bisacetal which is a 2,3-deacetylation product. The base is used in an amount of 1.0 to 5.0 mol, preferably 1.0 to 3.0 mol, per mol of the macrolide compound. A compound sulfonylated at the 4'-position can be produced from this compound by reacting it with the above-described sulfonylating agent in the presence of a base such as pyridine, collidine, lutidine, triethylamine or diisopropylethylamine in an inert solvent such as acetone, methyl ethyl ketone, dimethoxyethane, acetonitrile, toluene, dimethyl sulfoxide or dimethylformamide at −25° to 25° C.

Although the compound thus sulfonylated at the 4'-position can be isolated and purified prior to the subsequent reaction, it is preferably subjected to the halogenation reaction at the 4'-position thereof without the isolation, since this compound is relatively unstable. By the halogenation reaction conducted under the abovedescribed reaction conditions, the compound halogenated at the 4'-position, i.e. 2'-O-acyl-2,3-dehydro-3,4'-dideoxy-4'-halomycaminosyltylonolide bisacetal, can be obtained.

According to the production scheme 4-2, the halogenated compound can be obtained also by protecting the hydroxyl group at the 23-position of 9,20-bisacetal of the 2'-O-acyl-3-O-acetylmycaminosyltylonolide, then sulfonylating this compound at the 4'-position thereof under the above-described reaction conditions, halogenating the resultant compound under the above-described reaction conditions, and deacylating it under the above-described reaction conditions. Although the compound sulfonylted at the 4'-position can be isolated and purified prior to the subsequent reaction, it is preferably subjected to the subsequent reaction without the isolation, since the compound itself is relatively unstable.

When the 2'-O-acyl-2,3-dehydro-3,4'-dideoxy-4'-halomycaminosyltylonolide bisacetal produced as described above is dissolved in, for example, methanol or ethanol and catalytically reduced in the presence of a catalyst such as a Raney nickel and a base under a hydrogen pressure ranging from atmospheric pressure to about 4.0 kg/cm² under the above-described reaction conditions according to the production scheme 4-3, a corresponding 3,4'-dideoxymycaminosyltylonolide bisacetal is obtained. 3,4'-dideoxymycaminosyltylonolide can be produced by dissolving this compound in an organic solvent such as tetrahydrofuran, dioxane or acetone, and then treating it with dilute hydrochloric acid to conduct both deacetalization and removal of the protecting group at the 23-position.

EXAMPLES

The following Examples will further illustrate the present invention, which by no means limit the present invention.

Example 1

3,4'-Di-O-benzylsulfonyl-23-O-t-butyldimethylsilyl-mycaminosyltylonolide 9,20-bis(ethyleneacetal)

1.00 g (1.25 mmol) of 23-O-t-butyldimethylsilylmycaminosyltylonolide 9,20-bis(ethylneacetal) was dissolved in 20 ml of anhydrous pyridine. After cooling to −40° C., 0.67 g (3.51 mmol) of benzylsulfonyl chloride was added to the solution under stirring, and the reaction was conducted at −20° C. for 3 h. The reaction was confirmed by TLC, and terminated by addition of 0.67 ml of water. The temperature was returned to room temperature. Water was added to the reaction liquid and, one hour after, the reaction liquid was concentrated under reduced pressure. After extraction with chloroform, the chloroform layer was washed with saturated aqueous sodium hydrogencarbonate solution and then with saturated aqueous common salt solution. After dehydration over magnesium sulfate followed by filtration, the filtrate was concentrated to obtain 1.38 g (quantitative) of crude 3,4'-di-O-benzylsulfonyl-23-O-t-butyldimethylsilyl-mycaminosyltylonolide 9,20-bis(ethyleneacetal) in the form of a light yellow solid foam.

Example 2

3-O-Benzylsulfonyl-23-O-t-butyldimethylsilyl-4'-deoxy-4,-iodomycaminosyltylonolide 9,20-bis(ethyleneacetal):

415 mg (0.375 mmol) of the crude compound obtained in Example 1 was dissolved in 6.2 ml of anhydrous methyl ethyl ketone. After purging with nitrogen, 84 mg (0.560 mmol) of sodium iodide was added to the solution, and the resultant mixture was stirred under heating at 80° C. 30 min after, the reaction liquid was returned to room temperature and filtered. The filter cake was washed with acetone. The filtrate and the wash solution were combined together and concentrated. The concentrate was extracted with chloroform, washed successively with saturated aqueous sodium hydrogencarbonate solution, 10% sodium thiosulfate and saturated aqueous common salt solution, and then dehydrated over magnesium sulfate. After filtration followed by concentration of the filtrate, 410 mg of a light yellow syrup was obtained. The syrup was purified by silica gel column chromatography to obtain 300 mg (yield: 75%) of 3-O-benzylsulfonyl-23-O-t-butyldimethylsilyl-4'-deoxy-4'-iodomycaminosyltlonolide 9,20bis(ethyleneacetal) in the form of a colorless solid.

Specific rotation $[\alpha]^{27}_D$ −70° (Cl, CHCl$_3$)

| Elementary analysis for C$_{48}$H$_{78}$NO$_{13}$ISSi: | | | |
|---|---|---|---|
| | C | H | N | I (%) |
| Found | 54.09 | 7.27 | 1.08 | 11.95 |
| Calculated | 54.17 | 7.39 | 1.32 | 11.92 |

FAB-MS: 1064 (M + H)$^+$

Example 3

3-O-t-Butyldimethylsilyl-3,4'-dideoxymycaminosyltylonolide 9,20bis(ethyleneacetal)

296 mg (0.278 mmol) of the compound obtained in Example 2 was dissolved in 6 ml of methanol. 0.5 ml of Raney nickel was added to the solution. After purging with argon followed by addition of 116 mg (0.835 mmol) of potassium carbonate, hydrogen was blown thereinto for 3 h. After confirmation of the completion of the reaction by HPLC, the reaction liquid was filtered. After concentration of the filtrate followed by extraction with chloroform, the extract was washed with 1M aqueous potassium carbonate solution and then with saturated aqueous sommon salt solution. After dehydration over magnesium sulfate followed by filtration, the filtrate was concentrated to obtain 204 mg (95%) of a crude compound in the form of a colorless solid foam. The solid product was purifed by silica gel column chromatography to obtain 186 mg of 23-O-t-butyldimethylsilyl-3,4'-dideoxymycaminosyltylonolide 9,20-bis(ethyleneacetal) in the form of a colorless solid foam (yield: 87%).

$^1$H—NMR and mass spectrum of this product coincided with those of a standard sample synthesized by another route.

NMR(CDCl$_3$, TMS internal standard)

ε 0.88 (9H,s,t-butyl of, t-butyldimethylsylyl) 1.02(3H,d, H-21), 1.24(3H,d,H-6'), 1.74(3H,s,H-22) 2.29(6H,s, N(CH$_3$)$_2$-3'), 4.28(1H,d,H-1'), 5.37(1H,d,H-13), 5.61(1H,d,H-10), 6.39(1H,d,H-11)

FAB-MS: 768 (M+H)$^+$

Example 4

2'-O-Acetyl desmycosin 9,20-bis(ethyleneacetal)

23.7 g of 2'-O-acetyltylosin was suspended in 100 ml of toluene. 12.36 g (83.5 mmol) of ethyl orthoformate, 12.95 g (208.8 mmol) of ethylene glycol and 6.30 g (27.1 mmol) of camphorsulfonic acid were added to the resultant suspension to obtain a homogeneous solution. The solution was stirred at 50° C. for 2 h. Then the reaction solution was washed with 100 ml of 5% aquous sodium hydrogencarbonate solution, 100 ml of water and 10% aqueous common salt solution. The organic layer was dried over anhydrous sodium sulfate and then dried to solid under reduced pressure to obtain 20.20 g of the intended compound which was positive in sulfuric acid color reaction at Rf 0.49 on silica gel TLC with toluene/acetone (1/1) developer.

UV(MeOH)λ max: 235nm

IR(KBr) ν max: 3470,2975,2938,2882,1746,1236,1169, 1084,961 cm$^{-1}$

NMR(CDCl$_3$): (only main peaks)

ε:0.78 (3H, bs, H-18), 0.93 (3H, t, J=7.3 Hz, H-17), 1.01 (3H, d, J=6.6 Hz, H-Z1), 1.26 (3H, d, J=6.2 Hz, H-6"), 1.32 (3H, d, J=6.2 Hz, H-6'), 1.70 (3H, s, H-22), 2.01 (3H, s, OCOCH$_3$-2'), 2.39 (6H, s, N (CH$_3$)$_2$-3'), 3.05 (1H, t, J=9.5 Hz, H-4'), 3.18 (1H, bd, J=7. OHz, H-4"), 3.49 (3H, s, OCH$_3$-2"), 3.62 (3H, s, OCH$_3$-3"), 4.55 (1H, d, J=8.1 Hz, H-1"), 4.64 (1H, br, H-1'), 4.96 (1H, m, H-20), 4.96 (1H, m, H-15), 5.03 (1H, dd, J=10.6&7.7 Hz, H-2'), 5.42 (1H, d, J=10.6 Hz, H-13), 5.64 (1H, d, J=15.8 Hz, H-10), 6.37 (1H, d, J=15.8 Hz, H-11)

FAB-MS :902 (M+H)$^+$

Example 5

Production of 2'-O-acetyl-4"-O-trimethylsilyl desmycosin 9,20-bis(ethyleneacetal)

18.9 g (20.9 mmol) of 2'-O-acetyl desmycosin 9,20-bis(ethyleneacetal) was dissolved in 94 mol of toluene. 2.52 ml (31.2 mmol) of pyridine was added dropwise to the solution and the resultant mixture was cooled to –5° C. 3.42 ml (27 mmol) of trimethylsilane chloride was added to the solution and the reaction was conducted at that temperature for 80 min. The reaction liquid was washed with 150 ml of 5% aqueous hydrogencarbonate solution and 150 ml of 10% aqueous common salt solution and then dried over anhydrous sodium sulfate. The organic layer was concentrated under reduced pressure to obtain 20.64 g of the intended compound which was positive in sulfuric acid color reaction at Rf 0.57 on silica gel TLC with toluene/acetone (1/1) developer.

UV(MeOH)λ max: 235 nm

IR(KBr) ν max: 3520,2973,2884,1748,1713,1373,1236, 1171,1100,966,882,

NMR(CDCl$_3$): (only main peaks)

ε:0.17 (9H, s, Si (CH$_3$)$_3$), 0.77 (3H, bs, H-18), 0.91 (3H, t, J=7.3 Hz, H-17), 1.01 (3H, d, J=6.6 Hz, H-21), 1.18 (3H, d, J=6.2 Hz, H-6"), 1.32 (3H, d, J=5.9 Hz, H-6'), 1.69 (3H, d, J=0.7 Hz, H-22), 2.01 (3H, s, OCOCH$_3$-2'), 2.38 (6H, s, N (CH$_3$)$_2$-3'), 2.59 (1H, t, J=10.3 Hz, H-3 '), 3.05 (1H, t, J=9.9 Hz, H-4'), 3.28 (1H, dd, J=9.2&2.6 Hz, H-4"), 3.49 (3H, s, OCH$_3$-2"), 3.60 (3H, s, OCH$_3$-3"), 4.59 (1H, d, J=7.7 Hz, H-1"), 4.64 (1H, hr, H-1'), 4.95 (1H, m, H-20), 4.96 (1H, m, H-15), 5.03 (1H, dd, J=10.6&7.7 Hz, H-2'), 5.42 (1H, d, J=10.6 Hz, H-13), 5.62 (1H, d, J=15.8 Hz, H-10), 6.36 (1H, d, J=15.8 Hz, H-11)

FAB-MS: 974 (M+H)$^+$

Example 6

Production of 2',4"-di-O-acetyl desmycosin 9,20-bis(ethyleneacetal)

200 mg (0.222 mmol) of 2'-O-acetyl desmycosin 9.20-bis(ethyleneacetal) was dissolved in 2 ml of methylene chloride. 35.7 μl (0.444 mmol) of pyridine was added to the solution. 23.6 μl (0.333 mmol) of acetyl chloride was added to the resultant mixture under cooling with ice, and the reaction was conducted at that temperature for 1 h. 20 ml of methylene chloride was added to the reaction liquid and the resultant mixture was washed with 20 ml of 5% aqueous sodium hydro9encarbonate solution and 20 ml of saturated aqueous common salt solution, and then dried over anhydrous sodium sulfate. The organic layer was concentrated under reduced pressure, and 244 mg of the residue thus obtained was subjected to silica gel chromatography (10 g) and eluted with toluene/acetone (5/1). A fraction which was positive in sulfuric acid color reaction at Rf 0.45 on silica gel TLC with toluene/acetone (2/1) developer was taken to obtain 133 mg of the intended compound in the form of a colorless amorphous solid (yield: 64%).

UV(MeOH) λ max: 235 nm

IR(KBr) ν max: 3524,1745,1236,1088,1049cm$^{-1}$

NMR(CDCl$_3$): (only main peaks)

ε: 0.77(3H,bs,H-18), 0.92(3H,t,J=7.3 Hz,H-17) 1.00 (3H, d, J=6.6 Hz, H-21), 1.17 (3H, d, J=6.6 Hz, H-6"), 1.32 (3H, d, J=5.9 Hz, H-6'), 1.70 (3H, s, H-22), 2.01 (3H, s, OCOCH$_3$), 2.11 (3H, s, OCOCH$_3$), 2.39 (6H, s, N (CH$_3$)$_2$-3'), 2.59 (1H, t, J=10.3 Hz, H-3'), 2.89 (1H, m, H-14), 3.31 (1H, m, H-5'), 3.48 (3H, s, OCH$_3$-2"), 3.52 (3H, s, OCH$_3$-3"), 4.44 (1H, dd, J=2.9&9.5 Hz, H-4"), 4.61 (1H, d, J=8.1 Hz, H-1'), 5.03(1H,dd,J=10.3&7.3 Hz, H-2'), 5.40 (1H, d, J=10.3 Hz, H-13), 5.63 (1H, d, J=15.4 Hz, H-10), 6.36 (1H, d, J=15.4 Hz, H-11)

FAB-MS:944 (M+H)$^+$

Example 7

2'-O-acetyl-3,4'-di-O-methanesulfonyl-4"-O-trimethylsilyl desmycosin 9,20-bis(ethyleneacetal)

10.07 g (10.3 mmol) of 2'-O-acetyl-4"-O-trimethylsilyl desmycosin 9,20-bis(ethyleneacetal) was dissolved in 50 ml of toluene. Then 7.20 ml (51.7 mmol) of triethylamine was added to the solution and the resultant solution was cooled to –15° C. 2.8 ml (36.2 mmol) of methanesulfonyl chloride was added to the solution, and the reaction was conducted at –10° C for 1 h. 40 ml of toluene was added to the reaction liquid. The organic layer was washed with 80 ml of water, 40 ml of 5% aqueous sodium hydrogencarbonate solution and 40 ml of 10% aqueous common salt solution and then dried over anhydrous sodium sulfate. The organic layer was dried to solid under reduced pressure to obtain 12.94 g of the intended compound which was positive in sulfuric acid color reaction at Rf 0.55 on silica gel TLC with toluene/acetone (3/1) developer. This compound was immediately subjected to the subsequent reaction, since it was unstable. subsequent reaction, since it was unstable.

NMR(CDCl$_3$): (only main peaks)

ε:0.16 (9H, s, Si(CH$_3$)$_3$), 0.88 (3H, d, J=7.3 Hz, H-18), 0.92 (3H, t, J=7.3 Hz, H-17), 1.02 (3H, d, J=6.6 Hz, H-21), 1.18 (3H, d, J=6.2 Hz, H-6"), 1.35 (3H, d, J=5.9 Hz, H-6'), 1.69 (3H, d, J=0.7 Hz, H-22), 2.04 (3H, s, OCOCH$_3$-2'), 2.39 (6H, s, N (CH$_3$)$_2$-3'), 2.93 (1H, t, J=10.3 Hz, H-3'), 3.10 (3H, s, OSO$_2$CH$_3$), 3.14 (3H, s, OSO$_2$CH$_3$), 3.28 (1H, dd, J=9.5&2.6 Hz H-4"), 3.47 (3H, s, OCH$_3$-2"), 3.59 (3H, s, OCH$_3$-3"), 4.22 (1H, t, J=9.9 Hz, H-4'), 4.57(1H, d, J=7.7 Hz, H-1"), 4.60 (1H, br, H-1'), 4.75 (1H, br, H-3), 4.93(1H, m, H-15), 4.96 (1H, m, H-20), 5.03 (1H, dd, J=10.3&8.0 Hz, H-2'), 5.47 (1H, d, J=11.0 Hz, H-13), 5.54 (1H, d, J=15.8 Hz, H-10), 6.34 (1H, d, J=15.8 Hz, H-11)

FAB-MS: 1130 (M+ H)$^+$

Example 8

2',4"-Di-O-acetyl-3,4'-di-O-methanesulfonyl desmycosin 9,20-bis(ethyleneacetal)

109 mg (0.115 mmol) of 2',4"-di-O-acetyldesmycosin 9,20-bis(ethyleneacetal) was dissolved in 0.5 ml of toluene.80.2 ml (0.575 mmol) of triethylamine was added to the solution, and the resultant mixture was cooled with ice. 31.2 ml (0.403 mmol) of methanesulfonyl chloride was added to the mixture, and the reaction was conducted at that temperature for 1.5 h. 10 ml of ethyl acetate was added to the reaction liquid, and the resultant mixture was washed with 10 ml of 5% aqueous sodium hydrogencarbonate solution and 10 ml of saturated aqueous common salt solution, and then dried over anhydrous sodium sulfate. The organic layer was concentrated to dryness under reduced pressure to obtain 134 mg of the intended compound which was positive in sulfuric acid color reaction at Rf 0.64 on silica gel TLC with toluene/acetone (2/1) developer. This compound was immediately subjected to the subsequent reaction, since it was unstable.

NMR(CDCl$_3$): (only main peaks)

ε:0.88 (3H, d, J=7.3 Hz, H-18), 0.93 (3H, t, J=7.3 Hz, H-17), 1.03 (3H, d, J=6.8Hz, H-21), 1.17 (3H, d, J=6.2 Hz, H-6"), 1.36 (3H, d, J=5.9 Hz, H-6'), 1.70 (3H, s, H-22), 2.04 (3H, s, OCOCH$_3$), 2.11 (3H, s, OCOCH$_3$), 2.40 (6H, s, N (CH$_3$)$_2$-3'), 2.84 (1H, m, H-14), 2.94 (1H, t, J=10.3 Hz, H-3'), 3.04 (1H, dd, J=2.9&8.1 Hz, H-2"), 3.10 (3H, s, OSO$_2$CH$_3$), 3.12 (3H, s, OSO$_2$CH$_3$), 3.46 (3H, s, OCH$_3$-2"), 3.52 (3H, s, OCH$_3$-3"), 4.22 (1H, t, J=9.9 Hz, H-4'), 4.45 (1H, rid, J=2.6&9.9 Hz, H-4'), 4.60 (1H, d, J=8.1 Hz, H-1"), 5.03 (1H, dd, J=10.3&7.7 Hz, H-2'), 5.46 (1H, d, J=10.6 Hz, H-13), 5.55 (1H, d, J=15.6 Hz, H-10), 6.35 (1H, d, J=15.6 Hz, H-11)

FAB-MS: 1100(M+H)$^+$

Example 9

2'-O-acetyl-3,4'-di-O-benzylsulfonyl-4"-O-trimethylsilyl desmycosin 9,20-bis(ethyleneacetal)

1.0 g (1.03 mmol) of 2'-O-acetyl-4"-O-trimethylsilyl desmycosin 9,20-bis(ethyleneacetal) was dissolved in 10 ml of toluene.0.46 ml (3.4 mmol) of triethylamine was added to the solution, and the resultant mixture was cooled to −15° C. 430 mg (2.3 mmol) of benzylsulfonyl chloride was added to the solution, and the reaction was conducted at −10° C. for 1.5 h. 40 ml of toluene was added to the reaction liquid. The organic layer was washed with 50 ml of water, 50 ml of 5% aqueous sodium hydrogencarbonate solution and 50 ml of 10% aqueous common salt solution and then dried over anhydrous sodium sulfate. The organic layer was concentrated to dryness under reduced pressure to obtain 1.34 g of the intended compound which was positive in sulfuric acid color reaction at Rf 0.57 on silica gel TLC with toluene/acetone (4/1) developer. This compound was immediately subjected to the subsequent reaction, since it was unstable.

NMR(CDC$_3$): (only main peaks)

ε:0.16 (9H, s, Si(CH$_3$)$_3$), 0.81 (3H, d, J=7.3 Hz, H-18), 0.94 (3H, t, J=7.3 Hz, H-17), 1.01 (3H, d, J=6.6 Hz, H-21), 1.18 (3H, d, J=6.2 Hz, H-6"), 1.31 (3H, d, J=6.2 Hz, H-6'), 1.69 (3H, d, J=0.7 Hz, H-22), 1.99 (3H, s, OCD CH$_3$-2'), 2.47 (6H, s, N (CH$_3$)$_2$-3"), 2.94 (1H, t, J=10.3 Hz, H-3'), 3.29 (1H, dd, J=9.2&2.6 Hz, H-4'), 3.47 (3H, s, OCH$_3$-2"), 3.59 (3H, s, OCH$_3$-3"), 4.33 (1H, t, J=9.9 Hz, H-4'), 4.40 (1H, bd, J=15.0 Hz, OSO$_2$C HHph), 4.51 (1H, m, H-1'), 4.53 (2H, m, OSO$_2$CH$_2$ph), 4.57 (1H, m, SO$_2$CHHph), 4.58 (1H, d, J-8.1 Hz, H-1"), 4.87 (1H, br, H-3), 4.97 (1H, m, H-15), 5.03 (1H, dd, J=10.3&7.7 Hz, H-2'), 5.50 (1H, d, J=10.6 Hz, H-13), 5.55 (1H, d, J=15.8 Hz, H-10), 6.36 (1H, d, J=15.8 Hz, H-11), 7.36–7.42 (lOH, m, 2 x ph)

FAB-MS: 1282 (M+H)$^+$

Example 10

2'-O-Acetyl-4'-deoxy-4'-iodo-3-O-methanesulfonyl-4"-O-trimethylsilyl desmycosin 9,20-bis(ethyleneacetal)

12.94 g (11.5 mmol) of 2'-O-acetyl-3,4'-di-O-methanesulfonyl-4"-O-trimethylsilyl desmycosin 9,20-bis(ethyleneacetal) was dissolved in 60 ml of methyl ethyl ketone.2.58 g (17.2 mmol) of sodium iodide was added to the solution, and the reaction was conducted in a dark place at 85° C. for 1 h. The reaction liquid was cooled to room temperature to form precipitates, which were filtered and washed with 5 ml of toluene. The wash solution was combined with the mother liquor, and the resultant mixture was concentrated under reduced pressure. 60 ml of toluene and 60 ml of water were added to the concentrate to divide it into layers. Then the organic layer was washed with 40 ml of 10% sodium thiosulfate and 40 ml of water, dried over anhydrous sodium sulfate and concentrated to dryness under reduced pressure to obtain 10.73 g of the intended compound which was positive in sulfuric acid color reaction at Rf 0.51 on silica gel TLC with toluene/acetone (4/1) developer.

UV(MeOH) λ max: 235 nm

IR(KBr) ν max: 3443,2937,2940,2886,1746,1360,1233, 1173,1101,1049,966, 909,882,843 cm$^{-1}$ NMR(CDCl$_3$): (only main peaks)

ε:0.16 (9H, s, Si (CH$_3$)$_3$), 0.89 (3lt, d, J=7.3 Hz, H-18), 0.92 (3H, t, J=7.3 Hz, H-17), 1.02 (3H, d, J=7.0 Hz, H-21), 1.18 (3H, d, J=6.2 Hz, H-6"), 1.51 (3H, d, J=5.9 Hz, H-6'), 1.69 (3H, d, J=0.7 Hz, H-22), 2.02 (3H, s, OCOCH$_3$-2'), 2.42 (6H, s, N (CH$_3$)$_2$-3'), 3.12 (3H, s, OSO$_2$CH$_3$-3), 3.47 (3H, s, OCH$_3$-2"), 3.59 (3H, s, OCH$_3$-3"), 4.57 (1H, d, J=8.1 Hz, H-1"), 4.57 (1H, br, H-1'), 4.77 (1H, br, H-3), 4.91 (1H, dd, J=9.9&7.3 Hz,

H-2') 4.93 (1H, m, H-15), 4.98 (1H, br, H-20), 5.47 (1H, d, J=10.6 Hz, H-13), 5.54 (1H, d, J=15.8 Hz, H-10), 6.34 (1H, d, J=15.8 Hz, H-11)

FAS-MS: 1162 (M+H)$^+$

Example 11

2',4"-Di-O-acetyl-4'-deoxy-4'-iodo-3-O-methanesulfonyl desmycosin 9,20-bis(ethyleneacetal)

134 mg (0.115 mmol) of 2',4"-di-O-acetyl-3,4'-di-O-methanesulfonyl desmycosin 9,20-bis(ethyleneacetal) was dissolved in 1 ml of methyl ethyl ketone. 25.7 mg (0.173 mmol) of sodium iodide was added to the solution and the resultant mixture was heated under reflux for 30 min. ml of ethyl acetate was added to the reaction liquid. The obtained mixture was washed with 10 ml of 5% aqueous sodium hydrogencarbonate solution and 10 ml of saturated aqueous common salt solution, and then dried over anhydrous sodium sulfate. The organic layer was concentrated under reduced pressure and 128 mg of the obtained residue was purified by a dispensing silica gel TLC with toluene/acetone (3/1) developer. 86 mg (yield: 72%) of the intended compound which was positive in sulfuric acid color reaction at Rf 0.61 on TLC with the same developer was obtained from 2',4"-di-O-acetyl desmycosin 9,20-bis(ethyleneacetal) by two steps.

UV(MeOH) λ max: 234 nm

IR(KBr) ν max: 2975,2938,2884,1740,1377,1233,1171, 1088,1049,963,909 cm$^{-1}$

NMR(CDCl$_3$):
ε:0.89(3H, d,J=7.3 Hz, H-18), 0.92 (3H, t, J=7.3 Hz, H-17), 1.02 (3H, d, J=6.6 Hz, H-21), 1.17 (3H, d, J=5.9 Hz, H-6"), 1.51 (3H, d, J=5.9 Hz, H-6'), 1.70 (3H, s, H-22), 2.02 (3H, s, OCOCH$_3$), 2.11 (3H, s, OCOCH$_3$), 2.42 (6H, s, N(CH$_3$)$_2$ -3'), 3.04 (1H, dd, J=2.9&8.11 Hz, H-2"), 3.12 (3H, s, OSO$_2$CH$_3$-3), 3.46 (3H, s, OCH$_3$-2"), 3.52 (3H, s, OCH3-3"), 4.47 (1H, rid, J=2.9&11.7 Hz, H-4"), 4.60 (1H, d, J=8.1 Hz, H-1"), 5.46 (1H, d, J=11.0 Hz, H-13), 5.55 (1H, d, J=15.4 Hz, H-10), 6.35 (1H, d, J=15.4 Hz, H-11)

FAB-MS: 1134(M+H)$^+$

Example 12

2'-O-Acetyl-3-O-benzylsulfonyl-4'-deoxy-4'-iodo-4"-O-trimethylsilyl desmycosin 9,20-bis(ethyleneacetal):

1.23 g (0.96 mmol) of 2'-O-acetyl-3,4'-di-O-benzylsulfonyl-4"-Otrimethylsilyl desmycosin 9,20-bis(ethyleneacetal) was dissolved in 10 ml of methyl ethyl ketone. 216 mg (1.4 mmol) of sodium iodide was added to the solution, and the reaction was conducted in a dark place at 85° C. for 30 min. The reaction liquid was cooled to room temperature to form precipitates, which were filtered and washed with 5 ml of toluene. The wash solution was combined with the mother liquor, and the resultant mixture was concentrated under reduced pressure. 30 ml of toluene and 30 ml of water were added to the concentrate to divide it into layers. Then, the organic layer was washed with 30 ml of saturated aqueous sodium hydrogencarbonate solution and 30 ml of 10% aqueous common salt solution, dried over anhydrous sodium sulfate and concentrated to dryness under reduced pressure to obtain 1.22 g of the intended compound which was positive in sulfuric acid color reaction at Rf 0.51 on silica gel TLC with toluene/acetone (4/1) developer.

UV(MeOH) λ max: 235 nm

IR(KBr) ν max: 3488,2938,2886,1748,1456,1373,1233, 1171,1101,1049,968, 882 cm$^{-1}$ NMR(CDCl$_3$): (only main peaks)
ε:0.17 (9H, s, Si(CH$_3$)$_3$), 0.81 (3H, d, J=7.3 Hz, H-18), 0.93 (3H, t, J=7.3 Hz, H-17), 1.01 (3H, d, J=6.6 Hz, H-21), 1.18 (3H, d, J=6.2 Hz, H-6 "), 1.49 (3H, d, J=5.5 Hz, H-6'), 1.68 (3H, s, H-22), 1.97 (3H, s, OCOCH$_3$-2'), 2.41 (6H, s, N(CH$_3$)$_2$-3'), 2.78 (1H, t, J=10.3 Hz, H-3'), 3.48 (3H, s, OCH$_3$-2"), 3.59 (3H, s, OCH$_3$-3"), 4.40 (1H, m, H-1), 4.40 (1H, m, OSO$_2$CHHHph), 4.58 (1H, d, J=8.1 Hz, H-1"), 4.58 (1H, m, OSO$_2$CHHph), 4.87 (1H, dd, J=9.9&7.7 Hz, H-2'), 4.96 (1H, m, H-15), 5.51 (1H, d, J=11.4 Hz, H-13), 5.54 (1H, d, J=15.8 Hz, H-10), 6.36 (1H, d, J=15.8 Hz, H-11), 7.40 (5H, s, ph)

FAB-MS: 1238 (M+H)

Example 13

2'-O-Acetyl-3,4'-dideoxy desmycosin 9,20-bis(ethyleneacetal)

10.70 g (9.2 mmol) of 2'-O-acetyl-4'-deoxy-4'-iodo-3-O-methanesulfonyl-4"-O-trimethylsilyl desmycosin 9,20-bis(ethyleneacetal) was dissolved in 50 ml of methanol. 3.82 g (27.6 mmol) of potassium carbonate and then a suspension of 6.4 g (wet weight) (5 ml) of a Raney nickel (NDT-65; a product of Kawaken Fine Chemicals Co., Ltd.) in 8 ml of methanol were added to the solution to conduct the catalytic reduction under a hydrogen pressure of 3 kg/cm$^2$ for 2 h. The catalyst was filtered out through Celite, and the mother liquid was concentrated under reduced pressure. 100 ml of ethyl acetate and 100 ml of water were added to the concentrate to divide it into layers. The organic layer was washed with 100 ml of 20% aqueous common salt solution and then concentrated under reduced pressure. 0.86 ml of acetic anhydride was added to the concentrate to conduct the reaction at room temperature for 1.5 h. After washing with 30 ml of 5% aqueous sodium hydrogencarbonate solution and 30 ml of 20% aqueous common salt solution, the organic layer was dried over anhydrous sodium sulfate and then dried to solid under reduced pressure to obtain 7.46 g of the intended compound which was positive in sulfuric acid color reaction at Rf 0.44 on silica gel TLC with chloroform/toluene (10/1) developer.

303 mg of the intended compound was obtained from 480 mg of 2'-O-acetyl-3-O-benzylsulfonyl-4'-dioxy-4'-iodo-4"-O-trimethylsilyl desmycosin 9,20-bis(ethyleneacetal) by reduction followed by acetylation in the same manner as that described above.

71 mg of the intended compound was obtained from 100 mg of 2',4"-di-O-acetyl-4'-deoxy-4'-iodo-3-O-methanesulfonyl desmycosin 9,20-bis(ethyleneacetal) by reduction followed by acetylation in the same manner as that described above.

UV (MeOH) λ max: 235 nm

IR(KBr) ν max: 3476,2973,2938,2882,1744,1373,1238, 1167,1061,961cm $^{-1}$

NMR (CDCl$_3$): (only main peaks)
ε:0.82 (3H, bd, J=5.5 Hz, H-18), 0.92 (3H, t, J=7.3 Hz, H-17), 1.00 (3H, d, J=6.6 Hz, H-21), 1.23 (3H, d, J=6.2 Hz, H-6'), 1.26 (3H, d, J=6.2 Hz, H-6"), 1.35 (1H, m, H-4' a), 1.71 (1H, m, H-4" b), 1.73 (3H, d, J=1.1 Hz, H-22), 2.04 (3H, s, OCOCH$_3$-2'), 2.26 (GH, s, N(CH$_3$)$_2$-3'), 2.68 (1H, ddd, J=12.3&10.4&4.4 Hz, H-3'), 3.18 (1H, br, H-4"), 3.48 (3H, s, OCH$_3$-2"), 3.61 (3H, s, OCH$_3$-3"), 4.31 (1H, d, J=7.7 Hz, H-1'), 4.55 (1H, d, J=7.7 Hz, H-1"), 4.80 (1H, dd, J=10.4&?7.7 Hz, H-2'), 4.90 (1H, m, H-15), 4.95 (1H, bt, J=5.1 Hz, H-20), 5.42 (1H, d, J=10.6 Hz, H-13), 5.62 (1H, d, J=15.8 Hz, H-10), 6.36 (1H, d, J=15.8 Hz, H-11)

FAB-MS : 870 (M+H)$^+$

Example 14

2'-O-Acetyl-3,4'-dideoxy-4"-oxo desmycosin 9,20-bis(ethyleneacetal)

491 mg (3.68 mmol) of N-chlorosuccinimide was suspended in 8 ml of toluene, and the resultant suspension was cooled to 0° C. 0.4 ml (5.5 mmol) of dimethyl sulfide was added to the suspension and the resultant mixture was stirred at that temperature for 20 min. The resultant solution was cooled to –20° C., then 4 ml of a solution of 800 mg (0.92 mmol) of 2'-O-acetyl-3,4'-dideoxy desmycosin 9,20-bis(ethyleneacetal) in toluene was added to the resultant solution, and the reaction was conducted at that temperature for 1.5 h. 0.64 ml (4.6 mmol) of triethylamine was added to the reaction liquid and the reaction was conducted for additional 20 min. The reaction liquid was washed with 15 ml of 10% aqueous common salt solution twice, dried over anhydrous sodium sulfate and dried to solid under reduced pressure to obtain 755 mg of the intended compound which was positive in sulfuric acid color reaction at Rf 0.65 on silica gel TLC with chloroform/methanol (5/1) developer.

UV(MeOH) λ max: 235 nm

IR(KBr) ν max: 3441,2971,2938,2882,1744,1373,1240, 1169,1117,1057, 974 cm$^{-1}$ NMR(CDCl$_3$): (only main peaks)

ε:0.83 (3H, d, J=5.9 Hz, H-18), 0.94 (3H, t, J=7.3 Hz, H-17), 1.00 (3H, d, J=6.6 Hz, H-21), 1.24 (3H, d, J=5.9 Hz, H-6'), 1.35 (3H, d, J=7.0 Hz, H-6"), 1.38 (lit, m, H-4' a) , 1.73 (1H, m, H-4' b) 1.76 (3H, d, J=1.1 Hz, H-22), 2.04 (3H, s, OCOCH$_3$-2'), 2.26 (6H, s, N(CH$_3$)$_2$-3'), 3.46 (3H, s, OCH$_3$-2"), 3.50 (3H, s, OCH$_3$-3"), 3.74 (1H, t, J=3.3 Hz, H-2"), 4.17 (1H, q, J=7.0 Hz, H-5"), 4.26 (1H, d, J=3.7 Hz, H-3"), 4.32 (1H, d, J=7.7 Hz, H-1'), 4.81 (1H, dd, J=10.6&7.7 Hz, H-2'), 4.83 (1H, d, J=2.9 Hz, H-1"), 4.92 (1H, m, H-15), 4.95 (1H, bt, J=5.1 Hz, H-20), 5.39 (1H, d, J=10.3 Hz, H-13), 5.67 (1H, d, J=15.8 Hz, H-10), 6.37 (1H, d, J=15.8 Hz, H-11)

FAB-MS:868(M+H) $^+$

Example 15

3,4'-Dideoxymycaminosyltylonolide 9,20-bis (ethyleneacetal)

100 mg (0.115 mmol) of 2'-O-acetyl-3,4'-dideoxy-4"-oxo desmycosin 9,20-bis(ethyleneacetal) was dissolved in 1 ml of methanol. 0.115 ml of 1N-NaOH solution was added to the solution at 0 ° C., and the reaction was conducted at that temperature for 1 h.Then 40 μl of concentrated ammonia water was added to the reaction mixture and the temperature was elevated to conduct the reaction at 60° C. for 2 h. 5 ml of chloroform was added to the reaction liquid, and the organic layer was washed with 5 ml of 10% aqueous common salt solution four times. The organic layer was dried to solid under reduced pressure to obtain 74 mg of the intended compound which was positive in sulfuric acid color reaction at Rf 0.31 on silica gel TLC with chloroform/methanol (5/1 ) developer.

UV (MeOH) λ max: 235 nm

IR(KBr) λ max: 3449,2938,2880,1730,1642,1458,1381, 1169,1111,1049, 974 cm$^{-1}$ NMR(CDCl$_3$): (only main peaks)

ε:0.93 (3H, t, J=7.3 Hz, H-17), 0.99 (3H, d, J=6.6 Hz, H-18), 1.02 (3H, d, J=7.0 Hz, H-21), 1.24 (3H, d, J=5.9 Hz, H-6'), 1.78 (3H, d, J=1.1 Hz, H-22), 2.35 (6H, s, N(CH$_3$)$_2$-3'), 3.30 (1H, dd, J=10.3&7.3 Hz, H-2'), 4.29 (1H, d, J=7.0 Hz, H-1'), 4.84 (1H, m, H-15), 5.01 (1H, bt, J=5.1 Hz, H-20), 5.34 (1H, d, J=9.9 Hz, H-13), 5.66 (1H, d, J=15.8 Hz, H-10), 6.42 (1H, d, J=15.8 Hz, H-11)

FAB-MS:654 (M+H)$^+$ , 676 (M+Na)$^+$

Example 16

3,4'-Dideoxymycaminosyltylonolide 26 mg (0.05 mmol) of 3,4'-dideoxymycaminosyltylonolide 9,20-bis(ethyleneacetal) was dissolved in 0.2 ml of tetrahydrofuran. 0.2 ml of 1 N hydrochloric acid was added to the solution, and the reaction was conducted at room temperature for 1.5 h. The reaction liquid was diluted with water and then 3 ml of chloroform was added thereto. The organic layer was washed with 2 ml of 5% aqueous sodium hydrogencarbonate solution and 2 ml of 10% aqueous common salt solution and then dried over anhydrous sodium sulfate. The organic layer was dried to solid under reduced pressure to obtain 20 mg of the intended compound which was positive in sulfuric acid color reaction at Rf 0.25 on silica gel TLC with chloroform/methanol (5/1) developer.

UV(MeOH) λ max: 283 nm

IR (KBr) ν max: 3436,2967,2878,1725,1676,1591,1458, 1383,1316,1167,1071, 984 cm$^{-1}$ NMR (CDCl$_3$): (only main peaks) ε:0.94 (3H, t, J=7.3 Hz, H-17), 1.04 (3H, d, J=6.6 Hz, H-18), 1.20 (3H, d, J=6.2 Hz, H-6'), 1.21 (3H, d, J=6.6 Hz, H-21), 1.85 (3H, d, J=1.1 Hz, H-22), 2.29 (6H, s, N (CH$_3$)$_2$-3'), 2.90 (1H, m, H-14), 3.20 (1H, dd, J=7.3&10.3 Hz, H-2'), 4.19 (1H, d, J=7.3 Hz, H-1'), 4.88 (1H, m, H-15), 5.84 (1H, d, J=10.6 Hz, H-13), 6.35 (1H, d, J=15.6 Hz, H-10), 7.30 (1H, d, J=15.6 Hz, H-11), 9.69 (1H, s, H-20)

FAB-MS:566(M+H)$^+$

Example 17

3,2', 4"-Tri-O-acetyl desmycosin 9,20-bis(ethyleneacetal)

1.00 g (0.922 mmol) of 3,2',4",4"'-tetra-O-acetyltylosin was dissolved in 5 ml of toluene.0.61 ml (3.69 mmol) of ethyl orthoformate, 0.51 ml (9.22 mmol) of ethylene glycol and 321 mg (1.38 mmol) of dl-camphorsulfonic acid were successively added to the solution. After conducting the reaction at 50 ° C. for 2 h, 10 ml o f toluene was added to the reaction liquid. The resultant mixture was washed with 15 ml of 5% aqeous sodium hydrogencarbonate solution and 15 ml of saturated aqueous common salt solution and then dried over anhydrous sodium sulfate. The organic layer was concentrated under reduced pressure and the resultant concentrate was subjected to the silica gel chromatography (55 g) and eluted with toluene/acetone (5/1). A fraction which was positive in sulfuric acid color reaction at Rf 0.38 on silica gel TLC with toluene/acetone (2/1) developer was taken to obtain 525 mg (yield: 58%) of the intended compound in the form of a colorless amorphous solid.

UV (MeOH) λ max: 235 nm

IR(KBr) ν max: 3468,2976,2938,2882,1742,1372,1236, 1175,1086,1049 cm$^{-1}$

NMR(CDCl$_3$): (only main peaks)

ε: 0.84 (3H, hr, H-18), 0.90 (3H, t, J=7.3 Hz, H-17), 0.99 (3H, d, J=5.9 Hz, H-21), 1.16 (3H, d, J=6.6 Hz, H-6"), 1.31 (3H, d, J=5.9 Hz, H-6'), 1.71 (3H, s, H-22), 2.05 (3H, s, OCOCH$_3$), 2.11 (GH, s, 2×OCOCH$_3$), 2.39 (6H, s, N (CH$_3$)$_2$-3'), 2.91 (1H, m, H-14), 3.28 (1H, m, H-5'), 3.45 (3H, s, OCH$_3$-2"), 3.52 (3H, s, OCH$_3$-3"), 4.29 (1H, d, J=6.6 Hz, H-1'), 4.43 (1H, dd, J=2.2 & 10.3 Hz, H-4"), 4.60 (1H, d, J=8.1 Hz, H-1"), 4.81 (1H, m, H-15), 4.90 (1H, bs, H-20), 5.42 (1H, d, J=10.3 Hz, H-13), 5.61 (1H, d, J=16.1 Hz, H-10), 6.49 (1H, d, J=16.1 Hz, H-11)

FAB-MS: 986 (M+H)$^+$

Example 18

2',4"-Di-O-acetyl-2,3-dehydro-3-deoxy desmycosin 9,20-bis(ethyleneacetal)

100 mg (0 101 mmol) of 3,2',4"-tri-O-acetyl desmycosin 9,20-bis(ethyleneacetal) was dissolved in 1 ml of tetrahydrofuran. 9.7 mg (0.404 mmol) of sodium hydride was added to the solution under cooling with ice, and the reaction was conducted at room temperature for 1.5 h. 20 ml of ethyl acetate was added to the reaction liquid, and the resultant mixture was washed with water and dried over anhydrous sodium sulfate. The organic layer was concentrated under reduced pressure, and 110 mg of the concentrate thus obtained was purified by a dispensing silica gel TLC with toluene/acetone (2/1) developer to obtain 80 mg (yield: 85%) of the intended compound which was positive in sulfuric acid color reaction at Rf 0.49 on silica gel TLC with the same developer as above.

UV(MeOH) λ max: 218 nm

IR(KBr) ν max: 3468,2975,2938,2882,1746,1373,1235, 1171,1086,1051 cm$^{-1}$

NMR(CDCl$_3$): (only main peaks)

ε: 0.95 (3H, t, J=7.3 Hz, H-17), 1.17 (3H, d, J=6.6 Hz, H-6"), 1.33 (3H, d, J=6.6 Hz, H-6'), 1.70 (3H, s, H-22), 2.05 (3H, s, OCOCH$_3$), 2.11 (3H, s, OCOCH$_3$), 2.40 (GH, s, N (CH$_3$)$_2$-3'), 2.57 (1H, t, J=10.3 Hz, H-3'), 2.91 (1H, m, H-14), 3.33 (1H, m, H-5'), 3.48 (3H, s, OCH$_3$-2"), 3.52 (3H, s, OCH$_3$-3"), 4.62 (1H, d, J=8.1 Hz, H-1"), 4.87 (1H, m, H-15), 4.97 (1H, bs, H-20), 5.05 (1H, dd, J=7.3 & 10.3 Hz, H-2'), 5.33 (1H, d, J=10.3 Hz, H-13), 5.48 (1H, d, J=15.4 Hz, H-10), 5.54 (1H, d, J=15.4 Hz, H-2), 6.24 (1H, d, J=15.4 Hz, H-11), 6.70 (1H, dd, J=15.4 & 9.5 Hz, H-3)

FAB-MS: 926 (M+H)$^+$

Example 19

2',4"-Di-O-acetyl-2,3-dehydro-3-deoxy-4'-O-methanesulfonyl desmycosin 9,20-bis(ethyleneacetal)

50 mg (0.0539 mmol) of 2',4"-di-O-acetyl-2,3-dehydro-3-deoxy desmycosin 9,20-bis(ethyleneacetal) was dissolved in 0.5 ml of methyl ethyl ketone.22.5 μl (0.161 mmol) of triethylamine was added to the solution and then a solution of 6.3 μl (0.0808 mmol) of methanesulfonyl chloride in 100 μl of methyl ethyl ketone was added to the solution under cooling with ice to conduct the reaction at that temperature for 15 min. 10 ml of ethyl acetate was added to the reaction liquid and the resultant mixture was washed with 10 ml of 5% aqueous sodium hydrogencerbonate solution and 10 ml of saturated aqueous common salt solution, and then dried over anhydrous sodium sulfate. The organic layer was concentrated to solid under reduced pressure to obtain 55 mg of the intended compound which was positive in sulfuric acid color reaction at Rf 0.51 on silica gel TLC with toluene/acetone (4/1) developer.

NMR (CDCl$_3$): (only main peaks)

ε: 0.95 (3H, t, J=7.3 Hz, H-17), 1.17 (3H, d, J=6.6 Hz, H-6"), 1.38 (3H, d, J=5.9 Hz, H-6'), 1.70 (3H, s, H-22), 2.06 (3H, s, OCOCH$_3$), 2.11 (3H, s, OCOCH$_3$), 2.40 (6H, s, N (CH$_3$)$_2$-3'), 3.05 (1H, dd, J=8.1 & 2.9 Hz, H-2"), 3.11 (3H, s, OSO$_2$CH$_3$-4'), 3.48 (3H, s, OCH$_3$-2"), 3.52 (3H, s, OCH$_3$-3"), 4.24 (1H, t, J =9.5 Hz, H-4'), 4.82 (1H, d, J=8.1 Hz, H-1"), 5.08 (1H, dd, J=7.3 & 10.3 Hz, H-2'), 5.33 (1H, d, J=10.3 Hz, H-13), 5.48 (1H, d, J=15.4 Hz, H-10), 5.55 (1H, d, J=15.4 Hz, H-2), 6.24 (1H, d, J=15.4 Hz, H-11), 6.68 (1H, dd, J=15.4 & 9.5 Hz, H-3)

FAB-MS: 1004 (M+H)$^+$

Example 20

2',4"-Di-O-aeetyl-2,3-dehydro-3,4"-dideoxy-4'-iodo desmyeosin 9,20-bis(ethyleneacetal)

1.88 g (2.03 mmol) of 2',4"-Di-O-aeetyl-2,3-dehydro-3-deoxy desmycosin 9,20-bis(ethyleneacetal) was dissolved in 20 ml of methyl ethyl ketone. 0.85 ml (6.09 mmol) of triethylamine was added to the solution and then a solution of 0.20 ml (2.64 mmol) of methanesulfonyl chloride in 1.5 ml of methyl ethyl ketone was added to the resultant mixture under cooling with ice. After conducting the reaction at that temperature for 30 min, 907 mg (6.09 mmol) of sodium iodide was added to the reaction liquid, and the resultant mixture was heated under reflux for 30 min. The reaction liquid was concentrated under reduced pressure, and then 50 ml of ethyl acetate was added to the concentrate. After washing with 50 ml of 5% aqueous sodium hydrogencarbonate solution and 50 ml of saturated aqueous common salt solution followed by drying over anhydrous sodium sulfate, the organic layer was concentrated under reduced pressure and dried in vacuo to obtain 2.10 g of a colorless amorphous solid mainly comprising the intended compound.

UV(MeOH) λ max: 216 nm

IR(KBr) ν max: 2975,2936,2880,1750,1717,1373,1233, 1171,1090,1049 cm$^{-1}$

NMR(CDCl$_3$): (only main peaks)

ε:0.95 (3H, t, J=7.3 Hz, H-17), 1.17 (3H, d, J=6.6 Hz, H-6"), 1.53 (3H, d, J=5.1 Hz, H-6'), 1.69 (3H, s, H-22), 2.04(3H, s, OCOCH$_3$), 2.11 (3H, s, OCOCH$_3$), 3.05 (1H, dd, J=2.9 & 8.1 Hz, H-2"), 3.48 (3H, s, OCH$_3$-2"), 3.52 (3H, s, OCH$_3$-3"), 4.62 (1H, d, J=8.1 Hz, H-1"), 5.33 (1H, d, J=10.3 Hz, H-13), 5.47 (1H, d, J=15.4 Hz, H-10), 5.55 (1H, d, J=15.4 Hz, H-2), 6.24 (1H, d, J=15.4 Hz, H-11), 6.69 (1H, dd, J=15.4 & 9.5 Hz, H-3)

FAB-MS: 1036 (M+H)$^+$

Example 21

3,2',4"-Tri-O-acetyl-4'-O-methanesulfonyl desmycosin 9,20-bis(ethyleneacetal)

100 mg (0.101 mmol) of 3,2',4"-tri-O-acetyl-desmycosin 9, 20-bis(ethyleneacetal) was dissolved in 1 ml of methyl ethyl ketone. 63.1 μl (0.455 mmol) of triethylamine was added to the solution and then a solution of 30.5 μl (0.394 mmol) of methanesulfonyl chloride in 100 μl of methyl ethyl ketone was added to the resultant mixture under cooling with ice. After conducting the reaction at that temperature for 30 min, 10 ml of chloroform was added to the reaction liquid. After washing with 10 ml of 5% aqueous sodium hydrogencarbonate solution and 10 ml of saturated aqueous common salt solution followed by drying over anhydrous sodium sulfate, the organic layer was concentrated under reduced pressure and dried in vacuo to obtain 115 mg of a colorless amorphous solid mainly comprising the intended compound.

NMR(CDCl$_3$): (only main peaks)

ε: 0.84 (3H, br, H-18), 0.90 (3H, t, J=7.3 Hz, H-17), 0.99 (3H, d, J=5.9 Hz, H-21), 1.17 (3H, d, J=6.6 Hz, H-6"), 1.36 (3H, d, J=5.9 Hz, H-6'), 1.70 (3H, s, H-22), 2.06 (3H, s, OCOCH$_3$), 2.10 (3H, s, OCOCH$_3$), 2.11 (3H, s, OCOCH$_3$), 2.39 (6H, s, N (CH$_3$)$_2$-3'), 3.03 (1H, dd, J=2.9 & 8.1 Hz, H-2"), 3.10 (3H, s, OSO$_2$-CH$_3$-4'), 3.45 (3H, s, OCH$_3$-2"), 3.51 (3H, s, OCH$_3$-3"), 4.22 (1H, t, J=9.5 Hz, H-4'), 4.43 (1H, dd, J=2.2 & g.5 Hz, H-4"), 4.60 (1H, d, J=8.1 Hz, H-1"), 4.81 (1H, m, H-15), 4.88 (1H, t, J=5.1 Hz, H-20), 5.42 (1H, d, J=10.3 Hz, H-13), 5.61 (1H, d, J=16.1 Hz, H-10), 6.48 (1H, d, J=16.1 Hz, H-11),

FAB-MS: 1064 (M+H)$^+$

Example 22

3,2',4"-Tri-O-acetyl-4'-deoxy-4'-iodo desmycosin 9,20bis(ethyleneacetal)

100 mg (0.101 mmol) of 3,2',4"-tri-O-acetyl-desmycosin 9,20bis(ethyleneacetal) was dissolved in 1 ml of methyl ethyl ketone. 70.7 μl (0.507 mmol) of triethylamine was added to the solution and then a solution of 11.8 μl (0.152 mmol) of methanesulfonyl chloride in 0.1 ml of methyl ethyl ketone was added to the resultant mixture under cooling with ice. After stirring the resultant mixture at that temperature for 30 min to complete the mesylation reaction, 45.4 mg (0.303 mmol) of sodium iodide was added to the reaction liquid, and the resultant mixture was heated under reflux for 30 min. The reaction liquid was concentrated under reduced pressure, 20 ml of ethyl acetate was added thereto. After washing with 20 ml of 5% aqueous sodium hydrogencarbonate solution and 20 ml of water followed by drying over anhydrous sodium sulfate, the organic layer was concentrated under reduced pressure and dried in vacuo to obtain a concentrate. It was purified by a dispensing silica gel TLC with toluene/acetone (3/1) developer to obtain 98.5 mg (yield: 89%) of the intended compound which was positive in sulfuric acid color reaction at Rf 0.66 on TLC with the same developer.

UV(MeOH) λ max: 235 nm

IR(KBr) ν max: 2976,2938,2884,1744,1373,1235,1049 cm$^{-1}$

NMR(CDCl$_3$): (only main peaks)

ε: 0.85 (3H, br, H-18), 0.90 (3H, t, J=7.3 Hz, H-17), 0.99 (3H, d, J=6.2 Hz, H-21), 1.17 (314, d, J=6.2 Hz, H-6"), 1.51 (3H, d, J=5.5 Hz, H-6'), 1.71 (3H, d, J=1.1 Hz, H-22), 2.05(3H, s, OCOCH$_3$), 2.11 (6H, s, 2×OCOCH$_3$), 2.42 (6H, s, N(CH$_3$)$_2$-3'), 2.91 (1H, m, H-14), 3.03 (1H, rid, J=2.9 & 8.1 Hz, H-2"), 3.45 (3H, s, OCH$_3$-2"), 3.52 (3H, s, OCH$_3$-3"), 4.27 (1H, br, H-1'), 4.43 (1H, dd, J=2.6 & 9.9 Hz, H-4"), 4.60 (1H, d, J=8.1 Hz, H-1"), 4.82 (1H, m, H-15), 4.88 (1H, t, J=4.9 Hz, H-20), 4.94 (1H, dd, J=8.1 & 9.9 Hz, H-2'), 5.07 (1H, br, H-3), 5.42 (1H, d, J=10.3 Hz, H-13), 5.60 (1H, bd, J=15.8Hz, H-10), 6.50 (1H, d, J=15.8 Hz, H-11),

FAB-MS: 1096 (M+H)$^+$

Example 23

2',4"-Di-O-acetyl-2,3-dehydro-3,4'-dideoxy-4'-iodo desmycosin 9,20-bis(ethyleneacetal)

162 μl (2.28 mmol) of dimethyl sulfoxide and 27.4 mg (0.684 mmol) of sodium hydride were added to 6 ml of toluene to conduct the reaction at room temperature for 10 min. The resultant solution was cooled with ice, to which 500 mg (0.456 mmol) of 3,2',4"-tri-O-acetyl4'-deoxy-4'-iodo desmycosin 9,20-bis(ethyleneacetal) was added and the resultant mixture was stirred at room temperature for 2 h. 9.1 mg (0.228 mmol) of sodium hydride was added to the mixture to conduct the reaction at room temperature for 14 h. 10 ml of toluene was added to the reaction liquid. After washing with water followed by drying over anhydrous sodium sulfate, the organic layer was concentrated under reduced pressure and dried in vacuo to obtain 481 mg of an amorphous solid mainly comprising the intended compound which was positive in sulfuric acid color reaction at Rf 0.69 on silica gel TLC with toluene/acetone (4/1) developer.

UV(MeOH) λ max: 216 nm

IR(KBr) ν max: 2975,2936,2880,1750,1717,1373,1233, 1171,1090,1049 cm$^{-1}$

NMR(CDCl$_3$): (only main peaks)

ε: 0.95 (3H, t, J=7.3 Hz, H-17), 1.17 (3H, d, J=6.6 Hz, H-6"), 1.53 (3H, d, J=5.1 Hz, H-6'), 1.69 (3H, s, H-22), 2.04 (3H, s, OCOCH$_3$), 2.11 (3H, s, OCOCH$_3$), 2.43 (6H, s, N (CH$_3$)$_2$-3'), 3.05 (1H, dd, J=2.9 & 8.1 Hz, H-2"), 3.48 (3H, s, OCH$_3$-2"), 3.52 (3H, s, OCH$_3$-3"), 4.62 (1H, d, J=8.1 Hz, H-1"), 5.33 (1H, d, J=10.3 Hz, H-13), 5.47 (1H, d, J=15.4 Hz, H-10), 5.55 (1H, d, J=15.4 Hz, H-2), 6.24 (1H, d, J=15.4 Hz, H-11), 6.69 (1H, dd, J=15.4 & 9.5 Hz, H-3),

FAB-MS: 1036 (M+H)$^+$

Example 24

3,4'-Dideoxy desmycosin 9,20-bis(ethyleneacetal)

470 mg (0,454 mmol) of 2',4"-di-O-acetyl-2,3-dehydro-3,4'-dideoxy-4'-iodo desmycosin 9,20-bis(ethyleneacetal) was dissolved in 6 ml of methanol. 200 mg (1.45 mmol) of potassium carbonate was added to the solution and then a suspension of 400 mg (wet weight) (0.3 ml) of a Raney nickiel (NDT-65; a product of Kawaken Fine Chemicals Co., Ltd.) in 1 ml of methanol was added thereto.After conducting the catalytic reduction under a hydrogen pressure of 3.5 kg/cm$^2$ for 2 h, the catalyst was filtered off through Celite. The mother liquid was left to stand overnight and then concentrate under reduced pressure. 20 ml of ethyl acetate and 20 ml of water were added to the residue to divide it into layers.The organic layer was washed with 20 ml of saturated aqueous common salt solution and then dried over anhydrous sodium sulfate. The organic layer was concentrated under reduced pressure to obtain 423 mg of a residue, which was subjected to silica gel chromatography (40 g) with chloroform/methanol (25/1) eluent. A fraction which was positive in sulfuric acid color reaction at Rf 0.45 on silica gel TLC with chloroform/methanol (5/1) developer was taken to obtain 285 mg (yield: 76%) of a colorless amorphous solid.

UV(MeOH) λ max: 234 nm

IR(KBr) ν max: 3466,2971,2936,2880,1730,1379,1167, 1082 cm$^{-1}$

NMR(CDCl$_3$): (only main peaks)

ε: 0.93 (3H, t, J=7.3 Hz, H-17), 1.23 (3H, d, J=6.2 Hz, H-6'), 1.26 (3H, d, J=6.6 Hz, H-6'), 1.72 (3H, s, H-22), 2.28 (6H, s, N (CH$_3$)$_2$-3'), 2.86 (1H, m, H-14), 3.48 (3H, s, OCH$_3$-2"), 3.61 (3H, s, OCH$_3$-3"), 4.28(1H, d, J=7.3 Hz, H-1'), 4.54 (1H, d, J=7.7 Hz, H-1"), 4.91 (1H, m, H-15), 5.01 (1H, br, H-20), 5.42 (1H, d, J=10.6 Hz, H-13), 5.60 (1H, d, J=15.8 Hz, H-10), 6.39 (1H, d, J=15.8 Hz, H-11),

FAB-MS: 828 (M+H)$^+$

Example 25

2'-O-Acetyl-3',4'-dideoxy desmycosin 9,20-bis(ethyleneacetal)

285 mg of 3',4'-dideoxy desmycosin 9,20-bis(ethyleneacetal) was dissolved in 3.0 ml of ethyl acetate. 51.4 μl of acetic anhydride was added to the solution, and the reaction was conducted at room temperature for 3 h. 10 ml of ethyl acetate was added to the reaction liquid. After washing with 10 ml of 5% aqueous sodium hydrogencarbonate solution and 10 ml of 20% aqueous common salt solution, the organic layer was dried over anhydrous sodium sulfate and dryed to solid under reduced temperature to obtain 300 mg of the intended compound which was Dositive in sulfuric acid color reaction at Rf 0.44 on silica gel TLC with chloroform/methanol (10/1) developer.

UV(MeOH) λ max: 235 nm

IR(KBr) ν max: 3476,2973,2938,2882,1744,1373,1238, 1167,1061,961 cm$^-$

NMR(CDCl$_3$): (only main peaks)

ε: 0.82 (3H, bd, J=5.5 Hz, H-18), 0.92 (3H, t, J=7.3 Hz, H-17), 1.00 (3H, d, J=6.6 Hz, H-21), 1.23 (3H, d, J=6.2 Hz, H-6'), 1.26 (3H, d, J=6.2 Hz, H-6"), 1.35 (114, m, H-4'a), 1.71 (1H, m, H-4' b) 1.73 (3H, d, J=1.1 Hz, H-22), 2.04 (3H, s, OCOCH$_3$-2'), 2.26(6H, s, N (CH$_3$)$_2$-3'), 2.68 (1H, ddd, J=12.3 & 10.4 & 4.4 Hz, H-3"), 3.18 (1H, br, H-4"), 3.48 (3H, s, OCH$_3$-2"), 3.61 (3H, s, OCH$_3$-3") 4.31 (1H, d, J=7.7 Hz, H-1'), 4.55 (1H, d, J=7.7 Hz, H-1"), 4.80 (1H, dd, J=10.4 & 7.7 Hz, H-2'), 4.90 (1H, m, H-15), 4.95 (1H, bt, J=5.1 Hz, H-20), 5.42 (1H, d, J=10.6 Hz, H-13), 5.62 (1H, d, J=15.8 Hz, H-10), 6.36 (1H, d, J=15.8 Hz, H-11)

FAB-MS: 870 (M+H)$^+$

Example 26

3,2'-Di-O-acetyl-4"-O-isovaleryldemycinosyltylosin 48.4 g (55.7 mmol) of 3-O-acetyl-4"-O-isovaleryl demycinosyltylosin was dissolved in 200 ml of ethyl acetate. 6.3 ml (66.9 mmol) of acetic anhydride was added to the solution, and the reaction was conducted at room temperature for 2 h. The reaction liquid was washed with 200 ml of 5% aqueous sodium hydrogencarb0nate solution and 200 ml of 20% aqueous common salt solution, dried over anhydrous sodium sulfate and dried to solid under reduced pressure to obtain 50.7 g of the intended compound which was positive in sulfuric acid color reaction at Rf 0.66 on silica gel TLC with toluene/acetone (1/1) developer.

UV(MeOH) λ max: 282 nm

IR(KBr) ν max: 2973,2940,1740,1595,1373,1235,1169, 1057,1028 cm$^{-1}$

NMR(CDCl$_3$): (only main peaks)

ε:0.92(3H,t,J=7,3 Hz,H-17) 0.98(6H,d,J=6,6 Hz, dimethyl of isovaleryl) 1.84 (3H, s, H-22), 2.06 (3H, s, OCOCH$_3$-2'), 2.13 (3H, s, OCOCH$_3$-3), 2.41 (6H, s, N (CH$_3$)$_2$-3'), 4.24 (1H, d, J=7.7 Hz, H-1'), 4.62 (1H, d, J=10.3 Hz, H-4"), 5.01 (1H, dd, J=7.7 & 10.6 Hz, H-2'), 5.06 (1H, d, J=3.3 Hz, H-1"), 5.13 (1H, d, J=10.6 Hz, H-3), 5.90 (1H, d, J=10.3 Hz, H-13), 6.32 (1H, d, J=15.8 Hz, H-10), 7.40 (1H, d, J=15.8 Hz, H-11), 9.60 (1H, s, H-20)

FAB-MS: 910 (M+H)$^+$

Example 27

3,2'-Di-O-acetylmycaminosyltylonolide 450 ml of water was added to 50.7 g (55.7 mmol) of 3,2'-di-O-acetyl-4"-O-isovaleryldemycinosyltylosin, and the resultant mixture was stirred. An aqueous solution prepared by diluting 8.9 ml (167 mmol) of concentrated sulfuric acid with 50 ml of water was poured therein to dissolve the starting material. The temperature was then elevated to 50° C. 0.5 h after, the reaction liquid was cooled to 15° C. and washed with 300 ml of ethyl acetate three times. The aqueous layer was controlled at pH 5.8 with 20% aqueous sodium carbonate solution. After extraction with 300 ml of ethyl acetate twice, the extract was dried over anhydrous sodium sulfate and then dried to solid under reduced pressure to obtain 29.1 g of the intended compound which was positive in sulfuric acid color reaction on silica gel TLC at Rf 0.33 with toluene/acetone (2/1) developer.

UV (MeOH) λ max: 282 nm

IR (KBr) ν max: 2973,2938,1738,1593,1373,1236,1059 cm$^-$

NMR(CDCl$_3$): (only main peaks)

ε:0.92 (3 H, t, J=7.3Hz, H-17), 0.99 (3H, d, J:6.6 Hz, H-18), 1.22(3H, d, J:6.6 Hz, H-21), 1.28 (3H, d, J=6.2 Hz, H-6'), 1.84(3H, d, J=0.7 Hz, H-22), 2.06 (3H, s, OCOCH$_3$-2'), 2.15(3H, s, OCOCH$_3$-3), 2.40 (6H, s, N (CH$_3$)$_2$-3'), 2.93(1H, m, H-14), 3.03 (1H, t, J=9.5 Hz, H-4'), 3.50(1H, bd, J=8.8 Hz, H-5), 3.67 (1H, dd, J=7.0 & 10.6 Hz, H-23a), 3.72(1H, dd, J=4.4 & 10.6 Hz, H-23b), 4.29 (1H, d, J=7.7 Hz, H-1'), 4.79(1H, m, H-15), 4.99 (1H, dd, J=7.7 & 10.6 Hz, H-2'), 5.14 (1H, bd, J=10.6 Hz, H-10), 5.91 (1H, d, J=10.3 Hz, H-13), 6.31 (1H, d, J=15.8 Hz, H-10), 7.40 (1H, d, J=15.4 Hz, H-11), 9.61 (1H, s, H-20)

FAB-MS: 682 (M+H)$^+$

Example 28

3,2'-Di-O-acetylmycaminosyltylonolide 9,20-bis(ethyleneacetal)

9.74 g (51.2 mmol) of p-toluenesulfonic acid monohydrate was added to 100 ml of toluene, and the mixture was heated to distill off about 50 ml of toluene. After dehydration, the solution was cooled to or below, to which 28.4 ml (171 mmol) of ethyl orthoacetate and 23.8 ml (427 mmol) of ethylene glycol were added. The resultant solution was added to a cooled solultion of 29.1 g (42.7 mmol) of 3,2'-di-O-acetylmycaminosyltylonolide in 110 ml of toluene. The resultant mixture was stirred at room temperature for 1.5 h, then the temperature was gradually elevated to 50° C., and the reaction was conducted for 1 h. The reaction liquid was washed with 150 ml of 5% aqueous sodium hydrogencarbonate solution and 150 ml of 10% aqueous common salt solution, dried over anhydrous sodium sulfate and dried to solid under reduced pressure to obtain 30.48 g of the intended compound which was positive in sulfuric acid color reaction at Rf 0.55 on silica gel TLC with toluene/acetone (1/1) developer.

UV(MeOH) λ max: 235 nm

IR(KBr) ν max: 2975,2940,2882,1742,1373,1238,1182, 1055 cm$^{-1}$

NMR(CDCl$_3$): (only main peaks)

ε:0.85 (3H, br, H-18), 0.92 (3H, t, J=7.3 Hz, H-17), 1.00 (3H, d, J=6.6 Hz, H-21), 1.31 (3H, d, J=6.2 Hz, H-6'), 1.77 (3H, d, J=1.1 Hz, H-22), 2.05 (3H, s, OCOCH$_3$-2'), 2.13 (3H, s, OCOCH$_3$-3), 2.39 (6H, s, N (CH$_3$)$_2$-3'), 2.86 (1H, m, H-14), 3.05 (1H, t, J=9.5 Hz, H-4'), 3.57 (1H, dd, J=8.1 & 10.6 Hz, H-23a), 3.64 (1H, m, H-5), 3.69 (1H, dd, J=4.4 & 10.6 Hz, H-23b), 4.29 (1H, br, H-1'), 4.76 (1H, m, H-15), 4.91 (1H, m, H-20), 5.03 (1H, dd, J=7.7 & 10.6 Hz, H-2'), 5.06 (1H, br, H-3), 5.38 (1H, bd, J=10.6 Hz, H-13), 5.69 (1H, bd, J=15.4 Hz, H-10) 6.54 (1H, bd, J=15.4 Hz, H-11)

FAB-MS: 770 (M+H)$^+$

Example 29

3,2'-Di-O-acetylmycaminosyltylonolide 9,20-bis(ethyleneacetal)

27.9 g (0.147 mol) of p-toluenesulfonic acid monohydrate was added to 250 ml of toluene, and the mixture was heated to distill and dehydrated. The solution was cooled to 5° C. or below, to which 81.2 ml (0.488 mol) of ethyl orthoacetate and 68.1 ml (1.22 mmol) of ethylene glycol were added. The resultant solution was added to a cooled solultion of 111.1 g (0.122 mol) of 3,2'-di-O-acetyl-4"-O-isovaleryldemycinosyltylosin in 400 ml of toluene. The reaction liquid was gradually elevated to 50° C., and the reaction was conducted for 1.5 h. The reaction liquid was washed with 500 ml of 5% aqueous sodium hydrogencarbonate solution and 500 ml of 10% aqueous common salt solution twice, dried over anhydrous sodium sulfate and dried to solid under reduced pressure. The resultant residue was purified by silica gel column chromatography with toluene/acetone (3/1) developer to obtain 75.2 g of the intended compound which was the same as that of Example 28 in the form of an amorphous solid.

Example 30

3,2'-Di-O-acetyl-23-O-t-butyldimethylsilylmycaminosyltylonolide 9,20-bis(ethyleneacetal)

30.3 g (39.3 mmol) of 3,2'-di-O-acetylmycaminosyltylonolide 9,20-bis(ethyleneacetal) was dissolved in 150 ml of dimethylformamide. 4.04 g (59.4 mmol) of imidazole was added to the solution, and the resultant mixture was cooled to 0° C. 6.56 g (43.5 mmol) of t-butyldimethylsilyl chloride was added to the mixture under stirring and the reaction was conducted at room temperature for 2 h. 300 ml of toluene was added to the reaction liquid. After washing with 300 ml of 5% aqueous sodium hydrogencarbonate solution twice and 150 ml of water followed by drying over anhydrous sodium sulfate, the organic layer was dried to solid under reduced pressure to obtain 34.6 g of the intended compound which was positive in sulfuric acid color reaction at Rf 0.55 on silica gel TLC with toluene/acetone (2/1) developer.

UV(MeOH) λ max: 235 nm

IR(KBr) ν max: 2936,2884,1746,1373,1236,1084,1055, 837,777 cm$^{-}$

NMR(CDCl$_3$): (only main peaks)

ε:0.85(3H,br,H-18) 0.87 (9H, s,t-butyl of t-butyldimethylsilyl) 0.90 (3H, t, J=7.3 Hz, H-17), 1.00 (3H, d, J=6.6 Hz, H-21), 1.31 (3H, d, J=6.2 Hz, H-6'), 1.72 (3H, d, J=0.7 Hz, H-22, 2.05 (3H, s, OCOCH$_3$-2'), 2.12 (3H, s, OCOCH$_3$-3), 2.39 (SH, s, N (CH$_3$)$_2$-3'), 3.04 (1H, t, J=9.5 Hz, H-4'), 4.29 (1H, bd, J=6.2 Hz, H-1'), 4.83 (1H, m, H-15), 4.91 (1H, t, J=4.8 Hz, H-20), 5.03 (1H, dd, J=7.7 & 10.6 Hz, H-2') 5.06 (1H, br, H-3), 5.37 (1H, d, J=10.3 Hz, H-13), 5.63 (1H, bd, J=15.4 Hz, H-10), 6.50 (1H, hal, J=15.4 Hz, H-11)

FAB-MS: 884 (M+H)$^+$

Example 31

2'-O-Acetyl-23-O-t-butyldimethylsilyl-2,3-dehydro-3-deoxymycaminosyltylonolide 9,20-bis(ethyleneacetal)

2.34 g (58.6 mmol) of sodium hydride (60% in oil) was added to a mixed solvent comprising 100 ml of toluene and 13.9 ml (195 mmol) of dimethyl sulfoxide, and the resultant mixture was stirrred for 10 min. The reaction liquid was cooled to 0° C., and a solution of 34.5 g (39.0 mmol) of 3,2'-di-O-acetyl-23-O-t-butyldimethylsilylmyca minosyltylonolide 9,20-bis(ethyleneacetal) in 70 ml of toluene was added dropwise thereto. After conducting the reaction at that temperature for 1 h, 100 ml of water was added, and the mixture was controlled at pH 6 with 1 N-hydrochloric acid to divide it into layers. The organic layer was washed with 100 ml of 10% aqueous common salt solution, dried over anhydrous sodium sulfate and concentrated under reduced pressure to obtain 32.1 g of the intended compound which was positive in sulfuric acid color reaction at Rf 0.46 on silica gel TLC with toluene/acetone (3/1) developer.

UV(MeOH) λ max: 217 nm

IR(KBr) ν max: 2936,2881,1750,1717,1373,1232,1080, 1057,837,777 cm$^{-1}$

NMR(CDCl$_3$): (only main peaks)

ε:0.89(9H,s,t-butyl of t-butyldimethylsilyl) 0.95 (3H, t, J=7.3Hz, H-17), 1.34 (3H, d, J=6.2 Hz, H-6'), 1.71 (314, d, J=0.7 Hz, H-22), 2.06 (3H, s, OCOCH$_3$-2'), 2.44 (6H, s, N (CH$_3$)$_2$-3'), 3.11 (1H, t, J=9.2 Hz, H-4'), 4.44 (1H, d, J=7.3 Hz, H-1'), 4.90 (1H, m, H-15), 4.96 (1H, m, H-20), 5.06 (1H, dd, J=7.3 & 10.6 Hz, H-2'), 5.29 (1H, d, J=10.3 Hz, H-13), 5.51 (1H, d, J=15.8 Hz, H-10), 5.55 (1H, d, J=15.4 Hz, H-2), 6.25 (1H, d, J=15.8 Hz, H-11), 6.70 (1H, dd, J=9.5 & 15.4 Hz, H-11)

FAB-MS: 824 (M+H)$^+$

Example 32

2'-O-Acetyl-23-O-t-butyldimethylsilyl-2,3-dehydro-3,4'-dideoxy-4'-iodomycaminosyltylonolide 9,20-bis(ethyleneacetal)

31.8 g (38.6 mmol) of 2'-O-acetyl-23-O-t-butyldimethylsilyl-2,3-dehydro-3-deoxymycaminosyltylonolide 9,20-bis-(ethyleneacetal) was dissolved in 230 ml of methyl ethyl ketone. 10.8 ml (77.3 mmol) of triethylamine was added to the solution. Then a solution of 3.9 ml (50.2 mmol) of methanesulfonyl chloride in 15 ml of methyl ethyl ketone was added to the resultant mixture under cooling with ice. The reaction was conducted at that temperature for 1 h to obtain a mesylated compound [2'-O-acetyl-23-O-t-butyldimethylsilyl-2,3-dehydro-3-deoxy-4'-O-methanesulfonylmycaminosytylonolide 9,20-bis(ethyleneacetal)]. 17.4 g (116 mmol) of sodium iodide was added to the reaction liquid, and the temperature was elevated. After heating under reflux for 3 h to conduct the iodination, the reaction liquid was concentrated. 250 ml of toluene and 250 ml of water were added to the concentrate to divide it into layers. After washing with 250 ml of 10% sodium thiosulfate and 250 ml of 10% aqueous common salt solution followed by drying over anhydrous sodium sulfate, the organic layer was concentrated to dryness under reduced pressure to obtain 36.1 g of the intended compound which was positive in sulfuric acid color reaction at Rf 0.51 on silica gel TLC with toluene/acetone (10/1) developer.

2'-O-Acetyl-23-O-t-butyldimethylsilyl-2,3-dehydro-3-deoxy-4'-O-methanesulfonylmycaminosyltylonolide 9,20-bis(ethyleneacetal):

Rf: 0.55[toluene/acetone(6/1)]

NMR(CDCl$_3$): (only main peaks)

ε:0.89 (9H, s, t-butyl of t-butyldimethylsilyl) 0.95 (3H, t, J=7.3 Hz, H-17), 1.38 (3H, d, J=6.2 Hz, H-6'), 1.71 (3H, s, H-22), 2.06 (3H, s, OCOCH$_3$-2'), 2.40 (6H, s, N (CH$_3$)$_2$-3'), 2.89 (1H, t, J=10.3 Hz, H-3'), 3.11 (3H, s, OSO$_2$CH$_3$-4'), 4.24 (1H, t, J=9.5 Hz, H-4'), 4.42 (1H, d, J=10.3 Hz, H-1'), 5.08 (1H, dd, J=7.7 & 10.3 Hz, H-2'), 5.29 (1H, d, J=10.3 Hz, H-13), 5.50 (1H, d, J=15.8 Hz, H-10), 5.55 (1H, d, J=15.4 Hz, H-2), 6.24 (1H, d, J=15.8 Hz, H-11), 6.88 (1H, dd, J=9.5 & 15.4 Hz, H-3)

FAB-MS: 902 (M+H)$^+$

Intended compound:

UV(MeOH) λ max: 217 nm

IR(KBr) ν max: 2936,2882,1752,1715,1373,1231,1101, 1051,837,777 cm$^-$

NMR(CDCl$_3$): (only main peaks)

ε:0.89 (9H, s ,t-butyl of t-butyldimethylsilyl) 0.95 (3H, t, J=7.3 Hz, H-17), 1.53 (3H, d, J=5.5 Hz, H-6'), 1.71 (3H, d, J=0.7 Hz, H-22), 2.05 (3H, s, OCOCH$_3$-2'), 2.43 (6H, s, N (CH$_3$)$_2$-3'), 2.84 (1H, m, H-3'), 4.42 (1H, d, J=7.7 Hz, H-1'), 4.96 (1H, dd, J=7.7 & 9.9 Hz, H-2'), 5.29(1H, d, J=10.3 Hz, H-13), 5.50 (1H, d, J=15.8 Hz, H-10), 5.55(1H, d, J=15.4 Hz, H-2), 6.25 (1H, d, J=15.8 Hz, H-11), 6.69 (1H, dd, J=9.5 & 15.4 Hz, H-3)

FAB-MS: 934 (M+H)$^+$

Example 33

3,2'-di-O-Acetyl-23-O-t-butyldimethylsilyl-4'-O-methanesulfonylmycaminosyltylonolide 9,20-bis(ethyleneacetal)

50.0 mg (0.0565 mmol) of 3,2'-di-O-acetyl-23-O-t-butyldimethylsilylmycaminosyltylonolide 9,20-bis(ethyleneacetal) was dissolved in 1 ml of methyl ethyl ketone.35.4 μl (0.254 mmol) of triethylamine was added to the solution. Then a solution of 17.1 μl (0.220 mmol) of methanesulfonyl chloride in 50 ml of methyl ethyl ketone was added to the resultant mixture under cooling with ice. The resultant mixture was stirred at that temperature for 1 h, and 10 ml of chloroform was added to the reaction liquid. After washing with 10 ml of saturated aqueous sodium hydrogencarbonate solution and 10 ml of saturated aqueous common salt solution twice, the organic layer was concentrated to dryness under reduced pressure to obtain 53.9 mg of the intended compound which was positive in sulfuric acid color reaction at Rf 0.57 on silica gel TLC with toluene/acetone (5/1) developer.

NMR(CDCl$_3$): (only main peaks)

ε:0.84(3H,br,H-18) 0.87(9H,s,t-butyl of t-butylsilyl) 0.90 (3H, t, J=7.3 Hz, H-17), 0.99 (3H, d, J=6.6 Hz, H-21), 1.36 (3H, d, J=5.9 Hz, H-6'), 1.72 (3H, s, H-22), 2.06 (3H, s, OCOCH$_3$-2'), 2.11 (3H, s, OCOCH$_3$-3), 2.39 (6H, s, N (CH$_3$)$_2$-3'), 2.73 (1H, m, H-14), 3.10 (3H, s, OSO$_2$CH$_3$-4'), 3.43 (1H, m, H-5'), 4.22 (1H, t, J=9.5 Hz, H-4'), 5.37 (1H, d, J=10.3 Hz, H-13), 5.63 (1H, d, J=16.1 Hz, H-10), 6.49 (1H, d, J=16.1 Hz, H-11)

FAB-MS: 962 (M+H)$^+$

Example 34

3,2'-di-O-Acetyl-23-O-t-butyldimethylsilyl-4'-deoxy-4'-iodomycaminosyltylonolide 9,20-bis(ethyleneacetal):

266.1 mg (0.301 mmol) of 3,2'-di-O-acetyl-23-O-tbutyldimethylsilylmycaminosyltylonolide 9,20-bis(ethyleneacetal) was dissolved in 2 ml of methyl ethyl ketone. 62.9 μl (0.452 mmol) of triethylamine was added to the solution. Then a solution of 28.0 μl (0.361 mmol) of methanesulfonyl chloride in 70 μl of methyl ethyl ketone was added to the resultant mixture under cooling with ice. The resultant mixture was stirred at that temperature for 0.5 h to complete the mesylation reaction. 135.4 mg (0.903 mmol) of sodium iodide was added to the reaction liquid, and the temperature was elevated. After heating under reflux for 0.5 h to conduct the iodination, 10 ml of chloroform was added to the reaction liquid. After washing with 10 ml of saturated aqueous sodium hydrogencarbonate solution and 10 ml of saturated aqueous common salt solution twice followed by drying over anhydrous sodium sulfate, the organic layer was concentrated under reduced pressure and then the residue was purified by silica gel column chromatography with toluene/ethyl acetate (12/1) developer to obtain 210 mg (yield: 70%) of the intended compound which was positive in sulfuric acid color reaction at Rf 0.57 on silica gel TLC with toluene/acetone (10/1) developer.

UV(MeOH) λ max: 235 nm

IR(KBr) ν max: 2934,2882,1744,1372,1233,1179,1103, 1049 cm$^-$

NMR (CDCl$_3$): (only main peaks)

ε: 0.87 (9H, s, t-butyl of t-butyldimethylsilyl) 0.90 (3H, t, J=7.3 Hz, H-17), 0.99 (3H, d, J=6.6 Hz, H-21), 1.51 (3H, d, J=5.9 Hz, H-6'), 1.72 (3H, s, H-22), 2.05 (3H, s, OCOCH$_3$-2'), 2.12 (3H, s, OCOCH$_3$-3), 2.42 (6H, s, N (CH$_3$)$_2$-3'), 4.28 (1H, d, J=7.3 Hz, H-1'), 5.07 (1H, br, H-3), 5.37 (1H, d, J=11.0 Hz, H-13), 5.62 (1H, d, J=15.4 Hz, H-10), 6.50 (1H, d, J=15.4 Hz, H-11),

FAB-MS: 994 (M+H)$^+$

Example 35

2'-O-acetyl-23-O-t-butyldimethylsilyl-2,3-dehydro-3,4'-dideoxy-4'-iodomycaminosyltylonolide 9,20-bis(ethyleneacetal)

50.0 mg (0.0503 mmol) of 3,2'-di-O-acetyl-23-O-t-butyldimethylsilyl-4'-deoxy-4'-iodomycaminosyltylonolide 9,20-bis(ethyleneacetal) was dissolved in a mixed solvent comprising 0.5 ml of toluene and 35.7 μl (0.503 mmol) of dimethyl sulfoxide. 5.4 mg (0.226 mmol) of sodium hydride (60% in oil) was added to the solution, and the resultant mixture was stired for 20 h. 10 ml of ethyl acetate was added to the reaction liquid. After washing with 10 ml of water and 10 ml of saturated aqueous common salt solution twice, the organic layer was dried over anhydrous sodium sulfate and then concentrated under reduced pressure. The residue was purified by a dispensing silica gel TLC with toluene/acetone (10/1) developer to obtain 30 mg of the intended compound which was the same as that obtained in Example 32.

Example 36

23-O-t-butyldimethylsilyl-3,4'-dideoxymycaminosyltylonolide 9,20-bis(ethyleneacetal)

35.9 g (38.4 mmol) of 2'-O-acetyl-23-O-t-butyldimethylsilyl2,3-dehydro-3,4'-dideoxy-4'-iodomycaminosylthylonolide 9,20-bis(ethyleneacetal) was dissolved in 175 ml of methanol. 7.95 g (57.5 mmol) of potassium carbonate was added to the solution and then a suspension of 20 g a Raney nickiel (NDT-65; a product of Kawaken Fine Chemicals Co., Ltd.) in 30 ml of methanol was added thereto. After conducting the catalytic reduction under a hydrogen pressure of 3.5 kg/cm$^2$ for 2 h, the catalyst was filtered off through Celite. The filtrate was concentrated under reduced pressure. 200 ml of ethyl acetate was added to the residue. After washing with 200 ml of 20% aqueous common salt solution twice followed by drying over anhydrous sodium sulfate and drying to solid under reduced pressure, 28.0 g of the intended compound was obtained, which was positive in sulfuric acid color reaction at Rf 0.45 on silica gel TLC with chloroform/methanol (10/1) developer.

UV(MeOH) λ max: 235 nm
IR(KBr) ν max: 2938,2884,1734,1169,1111,1049,837,777 cm$^{-1}$
NMR(CDCl$_3$): (only main peaks)
ε:0.88(9H,s,t-butyl of t-butyldimethylsilyl) 0.92 (3H, t, J=7.3 Hz, H-17), 0.98 (3H, d, J=6.6 Hz, H-18), 1.02 (3H, d, J=7.0 Hz, H-21), 1.23 (3H, d, J=6.2 Hz, H-6'), 1.74 (3H, d, J=1.1 Hz, H-22), 2.27 (6H, s, N (CH$_3$)$_2$-3'), 3.26 (1H, dd, J=7.3 & 9.9 Hz, H-2'), 4.28 (1H, d, J=7.3 Hz, H-1'), 4.91 (1H, m, H-15), 5.01 (1H, m, H-20), 5.37 (1H, d, J=10.3 Hz, H-13), 5.61 (1H, d, J=15.8 Hz, H-10), 6.39 (1H, d, J=15.8 Hz, H-11)
FAB-MS: 768 (M+H)$^+$ Example 37

3,4'-Dideoxymycaminosyltylonolide 27.7 g (36.0 mmol) of 23-O-t-butyldimethylsilyl-3,4'-dideoxymycaminosyltylonolide 9,20-bis(ethyleneacetal) was dissolved in 150 ml of tetrahydrofuran. 300 ml of 1 N-hydrochloric acid was added to the solution, and the resultant mixture was stirred at room temperature for 1.5 h to conduct the hydrolysis reaction. 300 ml of water was added to the reaction liquid, and the resultant aqueous solution was washed with 150 ml of methylene chloride twice. pH of the aqueus layer was controlled at 6.0. After extraction with 300 ml of methylene chloride, the aqueous layer was again controlled at pH 6.0 and extracted with 300 ml of methylene chloride. The organic layers were combined together, washed with 300 ml of 20% aqueous common salt solution and dried over anhydrous sodium sulfate. The organic layer was dried to solid under reduced pressure to obtain 9.46 g of the intended compound.

This product had the same physicochemical properties as those of 3,4'-dideoxymycaminosyltylonolide described in Journal of Antibiotics (1992).

Industrial Applicability 3,4'-Dideoxymycaminosyltylonolide which can be produced by the process of the present invention is a substance having an antimicrobial activity-on Gram-positive and Gram-negative microorganisms in a broad range as described in J.P. KOKAI No. Hei 2-275894. In particular, it is useful as an antimicrobial agent, since it has an excellent effect of prevention from infection.

What is claimed is:

1. A compound of the following formula:

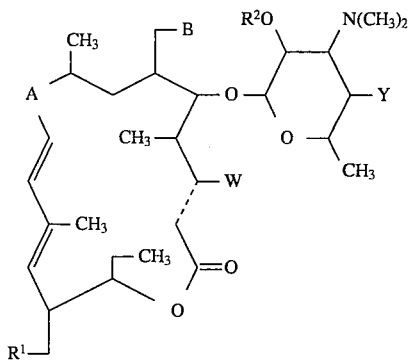

wherein

A represents a carbonyl group which is not protected or protected by dimethylacetal, diethylacetal, diethylthioacetal, ethyleneacetal or propyleneacetal;

B represents an aldehyde group which ie not protected or protected by dimethylacetal, diethylacetal, diethylthioacetal, ethyleneacetal or propyleneacetal;

R$^1$ represents a group of the following formula:

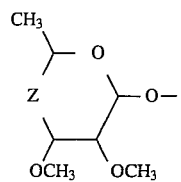

(Z being CHR$^4$ or C=O, and R$^4$ being a hydroxyl group which is not protected or protected by t-butyldimethylsilyl, dimethylhexylsilyl, trimethylsilyl, triethylsilyl, tri(t-butyl) silyl, trityl, tetrahydropyranyl, tetrahydrofuranyl, allyl, fluoroacetyl, difluoroacetyl, trifluoroacetyl, chloroacetyl, dichloroacetyl, trichloroacetyl, bromoacetyl, dibromoacetyl, methoxyacetyl, ethoxyacetyl, phenoxyacetyl, benzoyl, benzyl, methoxymethyl or benzyloxycarbonyl group)

R$^2$ represents a hydrogen atom or acyl group selected from the group consisting of formyl, acetyl, propionyl, butyryl, isobutyryl, valeryl, isovaleryl, pivaloyl, hexanoyl, benzoyl, toluoyl, xyloyl groups, phenylacetyl, phenylpropionyl and phenylhexanoyl groups;

W represents a hydrogen atom or sulfonyloxy group represented by the formula: —OSO$_2$ R$^3$ wherein R$^3$ represents methyl, ethyl, propyl, isopropyl, butyl, isobutyl, tert-butyl, pentyl, 1-methybutyl, 2-methylbutyl, neopentyl, trifluoromethyl, 2-oxo-10-bornanyl, phenyl, p-methoxyphenyl, p-nitrophenyl, p-fluorophenyl, o,p-difluorophenyl, pichlorophenyl, m-chlorophenyl, o-chlorophenyl, o,p-dichlorophenyl, p-bromophenyl, p-methylphenyl, m-methylphenyl, o,p-dimethylphenyl, m,p-dlmethylphenyl, naphthyl, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl or p-fluorobenzyl groups;

Y represents a halogen atom or sulfonyloxy group represented by the formula: —OsO₂ R³ wherein R³ represents methyl, ethyl, propyl, isopropyl, butyl, isobutyl, tert-butyl, pentyl, 1-methybutyl, 2-methylbutyl, neopentyl, trifluoromethyl, 2-oxo-10-bornanyl, phenyl, p-methoxyphenyl, p-nitrophenyl, p-fluorophenyl, o,p-difluorophenyl, p-chlorophenyl, m-chlorophenyl, o-chlorophenyl, o,p-dichlorophenyl, p-bromophenyl, p-methylphenyl, m-methylphenyl, o,p-dimethylphenyl, m,p-dimethylphenyl, naphthyl, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl or p-fluorobenzyl groups; and broken line "-------" represents a single bond.

2. A compound of the following formula:

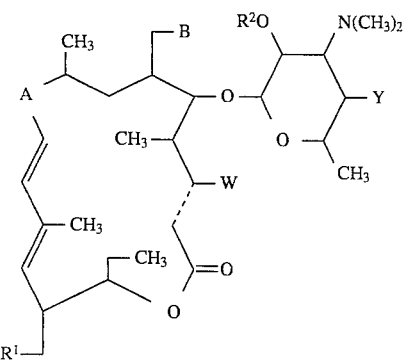

wherein

A represents a carbonyl group which is not protected or protected by dimethylacetal, diethylacetal, diethylthioacetal, ethyleneacetal or propyleneacetal;

B represents an aldehyde group which is not protected or protected by dimethylacetal, diethylacetal, diethylthioacetal, ethyleneacetal or propyleneacetal;

R¹ represents a group of the following formula:

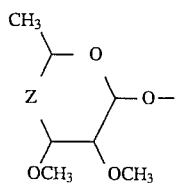

(Z being CHR⁴ or C=O, and R⁴ being a hydroxyl group which is not protected or protected by t-butyldimethylsilyl, dimethylhexylsilyl, trimethylsilyl, triethylsilyl, tri(t-butyl)silyl, trityl, tetrahydropyranyl, tetrahydrofuranyl, allyl, fluoroacetyl, difluoroacetyl, trifluoroacetyl, chloroacetyl, dichloroacetyl, trichloroacetyl, bromoacetyl, dibromoacetyl, methoxyacetyl, ethoxyacetyl, phenoxyacetyl, benzoyl, benzyl, methoxymethyl or benzyloxycarbonyl group);

R² represents a hydrogen atom or acyl group selected from the group consisting of formyl, acetyl, propionyl, butyryl, isobutyryl, valeryl, isovaleryl, pivaloyl, hexanoyl, benzoyl, toluoyl, xyloyl groups, phenylacetyl, phenylpropionyl and phenylhexanoyl groups;

W represents a hydrogen atom or a alkanoyloxy group which is selected from the group consisting of linear or branched alkanoyl groups having 1 to 6 carbon atoms;

Y represents a halogen atom or sulfonyloxy group represented by the formula: —OSO₂ R³ wherein R³ represents methyl, ethyl, propyl, isopropyl, butyl, isobutyl, tert-butyl, pentyl, 1-methybutyl, 2-methylbutyl, neopentyl, trifluoromethyl, 2-oxo-10-bornanyl, phenyl, p-methoxyphenyl, p-nitrophenyl, p-fluorophenyl, o,p-difluorophenyl, p-chlorophenyl, m-chlorophenyl, o-chlorophenyl, o,p-dichlorophenyl, p-bromophenyl, p-methylphenyl, m-methylphenyl, o,p-dimethylphenyl, m,p-dimethylphenyl, naphthyl, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl or p-fluorobenzyl group; and broken line "-------" represents a double bond when W is hydrogen atom and a single bond when W is an alkanoyloxy group selected from the group consLsting of linear or branched alkanoyl groups having 1 to 6 carbon atoms;

with the proviso that when Z is CHR⁴ and R² is said hydrogen atom, Y is said sulfonyloxy group.

3. A compound of the following formula:

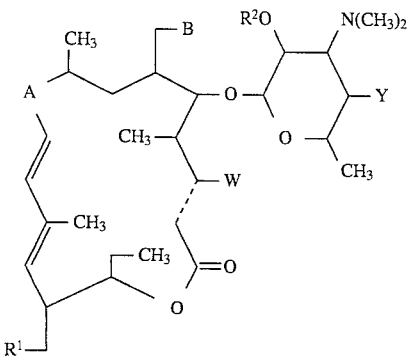

wherein

A represents a carbonyl group which is not protected or protected by dimethylacetal, diethylacetal, diethylthioacetal, ethyleneacetal or propyleneacetal;

B represents an aldehyde group which is not protected or protected by dimethylacetal, diethylacetal, diethylthioacetal, ethyleneacetal or propyleneacetal;

R¹ represents a hydroxyl group which is not protected or protected by t-butyldimethylilyl, dimethylhexylsilyl, trimethylsilyl, triethylsilyl, tri(t-butyl) silyl, trityl, tetrahydropyranyl, tetrahydrofuranyl, allyl, fluoroacetyl, difluoroacetyl, trifluoroacetyl, chloroacetyl, dichloroacetyl, trichloroacetyl, bromoacetyl, dibromoacetyl, methoxyacetyl, ethoxyacetyl, phenoxyacetyl, benzoyl, benzyl, methoxymethyl or benzyloxycarbonyl group, with the proviso that R¹ cannot be a group of the following formula:

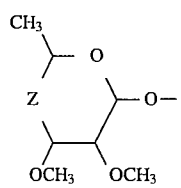

(Z being CHR⁴ or C=O, and R⁴ being a hydroxyl group which is not protected or protected by t-butyldimethylsilyl, dimethylhexylsilyl, trimethylsilyl, triethylsilyl, tri(t-butyl) silyl, trityl, tetrahydropyranyl, tetrahydrofuranyl, allyl, fluoroacetyl, difluoroacetyl, trifluoroacetyl, chloroacetyl, dichloroacetyl, trichloroacetyl, bromoacetyl, dibromoacetyl, methoxyacetyl, ethoxyacetyl, phenoxyacetyl, benzoyl, benzyl, methoxymethyl or benzyloxycarbonyl group);

$R^2$ represents a hydrogen atom or acyl group selected from the group consisting of formyl, acetyl, propionyl, butyryl, isobutyryl, valeryl, isovaleryl, pivaloyl, hexanoyl, benzoyl, toluoyl, xyloyl groups, phenylacetyl, phenylpropionyl and phenylhexanoyl groups;

W represents a hydrogen atom or alkanoyloxy group, selected from the group con2isting of linear or branched alkanoyl groups having 1 to 6 atoms;

Y represents a halogen atom, or sulfonyloxy group represented by the formula: —$OSO_2 R^3$ wherein $R^3$ represents methyl, ethyl, propyl, isopropyl, butyl, isobutyl, tert-butyl, pentyl, 1-methybutyl, 2-methylbutyl, neopentyl, trifluoromethyl, 2-oxo-10-bornanyl, phenyl, p-methoxyphenyl, p-nitrophenyl, p-fluorophenyl, o,p-difluorophenyl, p-chlorophenyl, m-chlorophenyl, o-chlorophenyl, dichlorophenyl, p-bromophenyl, p-methylphenyl, m-methylphenyl, o,p-dimethylphenyl, m,p-dimethylphenyl, naphthyl, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl or p-fluorobenzyl groups; and broken line "-------" represents a double bond when W is said hydrogen atom and a single bond when W is said slkanoyloxy group.

4. A process for producing a compound of the formula:

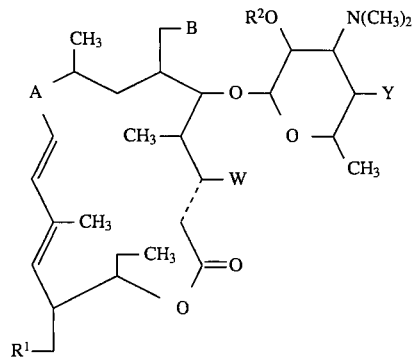

wherein

A represents a carbonyl group which is not protected or protected by dimethyiacetal, diethylacetal, diethylthioacetal, ethyieneacetal or propyleneacetal; B represents an aldehyde group which is not protected or protected by dimethylacetal, diethylacetal, diethylthioacetal, ethyleneacetal or propyleneacetal; $R^1$ represents a hydroxyl group which is not protected or protected by t-butyldimethylsilyl, dimethylhexylsilyl, trimethylsilyl, triethylsilyl, tri(t-butyl) silyl, trityl, tetrahydropyranyl, tetrahydrofuranyl, allyl, fluoroacetyl, difluoroacetyl, trifluoroacetyl, chloroacetyl, dichloroacetyl, trichloroacetyl, bromoacetyl, dibromoacetyl, methoxyacetyl, ethoxyacetyl, phenoxyacetyl, benzoyl, benzyl, methoxymethyl or benzyloxycarbonyl group); $R^2$ represents a hydrogen atom or acyl group selected from the group consisting of formyl, acetyl, propionyl, butyryl, isobutyryl, valeryl, isovaleryl, pivaloyl, hexanoyl, benzoyl, toluoyl, xyloyl groups, phenylacetyl, phenylacetyl, phenylpropionyl and phenylhexanoyl groups; W and Y each represent a hydrogen atom and broken line "-------" represents a single bond, by reducing a compound of,the above-described formula wherein A, B, $R^1$ and $R^2$ are as defined above, W represents a sulfonyloxy group represented by the formula: $OSO^2 R^3$ wherein $R^3$ represents methyl, ethyl, propyl, isopropyl, butyl, isobutyl, tert-butyl, pentyl, 1-methybutyl, 2-methylbutyl, neopentyl, trifluoromethyl, 2-oxo-10-bornanyl, phenyl, p-methoxyphenyl, p-nitrophenyl, p-fluorophenyl, o,p-difluorophenyl, p-chlorophenyl, m-chlorophenyl, o-chlorophenyl, o,p-dichlorophenyl, p-bromophenyl, p-methylphenyl, m-methylphenyl, o,p-dimethylphenyl, m,p-dimethylphenyl, naphthyl, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl or p-fluorobenzyl group; and Y. represents a halogen atom and broken line "-------" represents a single bond under an alkaline condition.

5. A process for producing a compound of the formula:

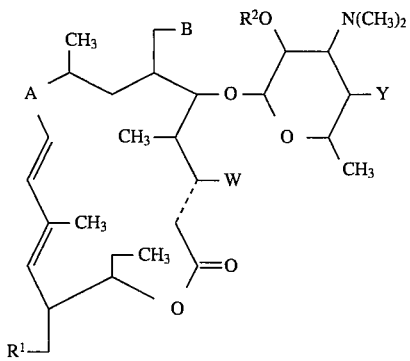

wherein

A represents a carbonyl group which is not protected or protected by dimethylacetal, diethylacetal, diethylthioacetal, ethyleneacetal or propyleneacetal; B represents an aldehyde group which is not protected or protected by dimethylacetal, diethylacetal, diethylthioacetal, ethyleneacetal or propyleneacetal; $R^1$ represents a hydroxyl group which is not protected or protected by t-butyldimethylsilyl, dimethylhexylsilyl, trimethylsilyl, triethylsilyl, tri(t-butyl)silyl, trityl, tetrahydropyranyl, tetrahydrofuranyl, allyl, fluoroacetyl, difluoroacetyl, trifluoroacetyl, chloroacetyl, dichloroacetyl, trichloroacetyl, bromoacetyl, dibromoacetyl, methoxyacetyl, ethoxyacetyl, phenoxyacetyl, benzoyl, benzyl, methoxymethyl or benzyloxycarbonyl group; $R^2$ represents a hydrogen atom or acyl group selected from the group consisting of formyl, acetyl, propionyl, butyryl, isobutyryl, valeryl, isovaleryl, pivaloyl, hexanoyl, benzoyl, toluoyl, xyloyl groups, phenylacetyl, phenylacetyl, phenylpropionyl and phenylhexanoyl groups; W and Y each represent a hydrogen atom and broken line "-------" represents a single bond, which comprises the steps of reacting a compound of the above-described formula wherein A, B, $R^1$ and $R^2$ are as defined above, W and Y each represent a hydroxyl group and broken line "-------" represent a single bond with a sulfonylating agent to form a compound of the above-described formula wherein A, B, $B^1$ and $B^2$ are as defined above, W and Y each represent sulfonyloxy group represented by the formula: $OSO^2 R^3$ wherein $R^3$ represents methyl, ethyl, propyl, isopropyl, butyl, isobutyl, tert-butyl, pentyl, 1-methybutyl, 2-methylbutyl, neopentyl, trifluoromethyl, 2-oxo-10-bornanyl, phenyl, p-methoxyphenyl, p-nitrophenyl, p-fluorophenyl, o,p-difluorophenyl, p-chlorophenyl, m-chlorophenyl, o-chlorophenyl, o,p-dichlorophenyl, p-bromophenyl, p-methylphenyl, m-methylphenyl, o,p-dimethylphenyl, m,p-dimethylphenyl, naphthyl, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl or p-fluorobenzyl group; and broken line "-------" represents a single bond;

reacting the resultant compound with a halogenating agent to form a compound of the above-described formula wherein A, B, $R^1$ and $R^2$ are as defined above, W represents said sulfonyloxy group, Y represents a halogen atom and broken line "-------" represents a single bond; and reducing the resultant compound under an alkaline condition to form the product compound.

6. A process for producing 3,4'-dideoxymycaminosyltylonolide or a salt thereof which comprises steps of reacting a compound of the formula:

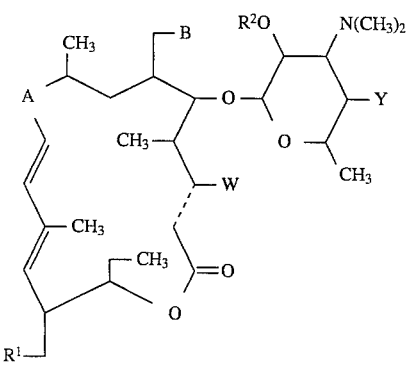

wherein

A represents a carbonyl group which is not protected or protected by dimethylacetal, diethylacetal, diethylthioacetal, ethyleneacetal or propyleneacetal; B represents an aldehyde group which is not protected or protected by dimethylacetal, diethylacetal, diethylthioacetal, ethyleneaoetal or propyleneacetal; $R^1$ represents a hydroxyl group which is not protected or protected by t-butyldimethylsilyl, dimethylhexylsilyl, trimethylsilyl, triethylsilyl, tri(t-butyl)silyl, trityl, tetrahydropyranyl, tetrahydrofuranyl, allyl, fluoroacetyl, difluoroacetyl, trifluoroacetyl, chloroacetyl, dichloroacetyl, trichloroacetyl, bromoacetyl, dibromoacetyl, methoxyacetyl, ethoxyacetyl, phenoxyacetyl, benzoyl, benzyl, methoxymethyl or benzyloxycarbonyl group); $R^2$ represents a hydrogen atom or acyl group selected from the group consisting of formyl, acetyl, propionyl, butyryl, isobutyryl, valeryl, isovaleryl, pivaloyl, hexanoyl, benzoyl, toluoyl, xyloyl groups, phenylacetyl, phenylacetyl, phenylpropionyl and phenylhexanoyl groups; W and Y each represent a hydrogen atom and broken line "-------" represents a single bond, with a sulfonylating agent to form a compound of the above-described formula wherein A, B, $R^1$ and $R^2$ are as defined above, W and Y each represent a sulfonyloxy group, represented by the formula: $OSO^2 R^3$ wherein $R^3$ represents methyl, ethyl, propyl, isopropyl, butyl, isobutyl, tert-butyl, pentyl, 1-methybutyl, 2-methylbutyl, neopentyl, trifluoromethyl, 2-oxo-10-bornanyl, phenyl, p-methoxyphenyl, p-nitrophenyl, p-fluorophenyl, o,p-difluorophenyl, p-chlorophenyl, m-chlorophenyl, o-chlorophenyl, o,p-dichlorophenyl, p-bromophenyl, p-methylphenyl, m-methylphenyl, o,p-dimethylphenyl, m,p-dimethylphenyl, naphthyl, benzyl, p-nitrobenzyl, o,p-dinitrobenzyl, p-chlorobenzyl, m-chlorobenzyl, p-methylbenzyl, m-methylbenzyl, o-methylbenzyl, o,p-dimethylbenzyl, p-methoxybenzyl or p-fluorobenzyl group; and broken line "-------" represents a single bond;

reacting the resultant compound with a halogenating agent to form a compound of the above-described formula wherein A, B, $R^1$ and $R^2$ are as defined above, W represents said sulfonyloxy group, Y represents a halogen atom and broken line "-------" represents a single bond;

reducing the resultant compound under an alkaline condition to form the compound of the above-described formula wherein A, B, $R^1$ and $R^2$ are as defined above, w and Y each represent a hydrogen atom and broken line "-------" represents a single bond; and removing the protecting group from the thus-obtained compound.

7. The process of claim 5 wherein said sulfonylating agent is methanesulfonyl chloride or benzylsulfonyl chloride.

8. The process of claim 6 wherein said sulfonylating agent is methanesulfonyl chloride or benzylsulfonyl chloride.

9. The process of claim 5 wherein said halogenating agent is sodium iodide.

10. The process of claim 6 wherein said halogenating agent is sodium iodide.

* * * * *